United States Patent
Spencer et al.

(10) Patent No.: US 12,226,197 B2
(45) Date of Patent: *Feb. 18, 2025

(54) OPAQUE SPLITS EMBEDDED IN TRANSPARENT MEDIA FOR OPTICAL EMITTER/DETECTOR ISOLATION

(71) Applicant: Apple Inc., Cupertino, CA (US)

(72) Inventors: Maegan K. Spencer, Emerald Hills, CA (US); Brian R. Land, Woodside, CA (US); Naoto Matsuyuki, Kasugai (JP); Erik L Wang, Redwood City, CA (US); William C. Lukens, San Francisco, CA (US); Steven C. Roach, San Francisco, CA (US)

(73) Assignee: APPLE INC., Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/462,603

(22) Filed: Sep. 7, 2023

(65) Prior Publication Data

US 2023/0414122 A1 Dec. 28, 2023

Related U.S. Application Data

(63) Continuation of application No. 16/811,783, filed on Mar. 6, 2020, now Pat. No. 11,786,139.

(Continued)

(51) Int. Cl.
*A61B 5/024* (2006.01)
*A61B 5/00* (2006.01)
(Continued)

(52) U.S. Cl.
CPC .......... *A61B 5/02438* (2013.01); *A61B 5/681* (2013.01); *G06F 1/163* (2013.01); *H01L 31/101* (2013.01)

(58) Field of Classification Search
CPC ... G06F 1/163; H01L 31/101; A61B 5/02438; A61B 5/681
See application file for complete search history.

(56) References Cited

U.S. PATENT DOCUMENTS 3,769,974 A 11/1973 Smart et al.
4,880,304 A 11/1989 Jaeb et al.
(Continued)

FOREIGN PATENT DOCUMENTS

CN 103625293 A 3/2014
CN 105765722 A 7/2016
(Continued)

*Primary Examiner* — Alyssa M Alter
*Assistant Examiner* — Jessandra F Hough
(74) *Attorney, Agent, or Firm* — Dorsey & Whitney LLP

(57) ABSTRACT

An electronic device can include a housing defining an aperture and at least partially defining an internal volume of the electronic device, an electromagnetic radiation emitter and an electromagnetic radiation detector disposed in the internal volume, and an optical component disposed in the aperture. The optical component can include a first and second transparent portions disposed above the electromagnetic radiation detector and the electromagnetic radiation emitter, and an opaque portion disposed between the first and second transparent portions and extending a thickness of the optical component. The first transparent portion, the second transparent portion, and the opaque portion can define a flush exterior surface of the electronic device.

20 Claims, 17 Drawing Sheets

Related U.S. Application Data

(60) Provisional application No. 62/898,858, filed on Sep. 11, 2019.

(51) Int. Cl.
*G06F 1/16* (2006.01)
*H01L 31/101* (2006.01)

(56) References Cited

U.S. PATENT DOCUMENTS

| | | |
|---|---|---|
| 6,444,076 B1 | 9/2002 | Herndon et al. |
| 7,067,893 B2 | 6/2006 | Mills et al. |
| 9,226,663 B2 | 1/2016 | Fei |
| 10,207,387 B2 | 2/2019 | Matsuyuki et al. |
| 2011/0004106 A1 | 1/2011 | Iwamiya et al. |
| 2012/0197093 A1 | 8/2012 | Leboeuf et al. |
| 2014/0070957 A1 | 3/2014 | Longinotti-Buitoni et al. |
| 2014/0185268 A1 | 7/2014 | Charle et al. |
| 2014/0288435 A1 | 9/2014 | Richards et al. |
| 2016/0061726 A1 | 3/2016 | Ness et al. |
| 2016/0360971 A1 | 12/2016 | Gross et al. |
| 2018/0014781 A1 | 1/2018 | Clavelle et al. |

FOREIGN PATENT DOCUMENTS

| | | |
|---|---|---|
| CN | 108511538 A | 9/2018 |
| EP | 3007037 A1 | 4/2016 |
| WO | 2013151507 A1 | 10/2013 |
| WO | 2015076750 A1 | 5/2015 |

OPAQUE SPLITS EMBEDDED IN TRANSPARENT MEDIA FOR OPTICAL EMITTER/DETECTOR ISOLATION

CROSS-REFERENCE TO RELATED APPLICATION(S)

This is a continuation of U.S. patent application Ser. No. 16/811,783, filed 6 Mar. 2020, and entitled "OPAQUE SPLITS EMBEDDED IN TRANSPARENT MEDIA FOR OPTICAL EMITTER/DETECTOR ISOLATION," which claims priority to U.S. Provisional Patent Application No. 62/898,858, filed 11 Sep. 2019, and entitled "OPAQUE SPLITS EMBEDDED IN TRANSPARENT MEDIA FOR OPTICAL EMITTER/DETECTOR ISOLATION," the entire disclosures of which are hereby incorporated by reference.

FIELD

The described embodiments relate generally to electronic devices. More particularly, the present embodiments relate to electronic devices including input components and output components.

BACKGROUND

As portable electronic devices continue to include increasingly greater numbers of features, integration of those features into a single device becomes ever more complex. For example, certain features can require both the emission of light from the electronic device, and the detection of light from the ambient environment. Components designed to emit light from the device can, however, also undesirably emit light that travels along a pathway incident on a light detector without ever reaching an ambient environment outside the device. These undesirable light pathways can cause false positives or undesirable amounts of noise when attempting to detect light from outside the device. Accordingly, it is desirable to provide components, such as a device enclosure, that can provide emitter and detector components with a desired level of optical isolation without undesirably increasing the size of the device.

SUMMARY

According to some aspects of the present disclosure, an electronic device can include a housing defining an aperture, and at least partially defining an internal volume of the electronic device, an electromagnetic radiation emitter and an electromagnetic radiation detector disposed in the internal volume, and a unitary optical component disposed in the aperture and separate from the electromagnetic radiation emitter and the electromagnetic radiation detector. The unitary optical component can include a first transparent portion overlying the electromagnetic radiation detector, a second transparent portion overlying the electromagnetic radiation emitter, and an opaque portion disposed between the first and second transparent portions extending a thickness of the unitary optical component. The first transparent portion, the second transparent portion, and the opaque portion can define an exterior surface of the electronic device and can be flush with respect to one another at the exterior surface.

In some examples, the electromagnetic radiation emitter is a light emitting diode. The electromagnetic radiation detector can detect visible light. The electromagnetic radiation detector can detect infrared light. The electronic device can further include at least one additional electromagnetic radiation emitter disposed under the second transparent portion. The electronic device can further include an isolation component disposed in the internal volume abutting the unitary optical component. The isolation component can at least partially define a first chamber and a second chamber, wherein the electromagnetic radiation detector is disposed in the first chamber and the electromagnetic radiation emitter disposed in the second chamber. The isolation component can isolate the electromagnetic radiation detector from electromagnetic radiation emitted by the electromagnetic radiation emitter within the internal volume. Electromagnetic radiation emitted by the electromagnetic radiation emitter must pass entirely through the second transparent portion and the first transparent portion to be detected by the electromagnetic radiation detector.

According to some aspects, a housing for an electronic device can include a body defining an aperture and at least partially defining an exterior surface of the electronic device, a unitary optical component disposed in the aperture including a first transparent portion, a second transparent portion surrounding the first transparent portion, a first opaque portion extending a thickness of the unitary optical component disposed between the first and second transparent portion, a third transparent portion, and a second opaque portion extending the thickness of the unitary optical component disposed between the second transparent portion and the third transparent portion. The first, second, and third transparent portions and the first and second opaque portions can further define the exterior surface of the electronic device, wherein the first, second, and third transparent portions define a larger portion of the exterior surface than the first and second opaque portions.

In some examples, the second transparent portion can surround the third transparent portion. The second opaque portion can surround the third transparent portion. The third transparent portion can surround the second transparent portion. The first, second, and third transparent portions and the first and second opaque portions can include ceramic material. The first, second, and third transparent portions and the first and second opaque portions can include polymeric material. At least one of the first, second, and third transparent portions can be joined to at least one of the first and second opaque portions by an adhesive. At least one of the first, second, and third transparent portions can be directly fused to at least one of the first and second opaque portions. At least one of the first opaque portion and the second opaque portion can include a non-planar sidewall. At least one of the first and second opaque portions can include a first section defining the exterior surface, and a second section defining an interior surface, the first and second sections being laterally offset relative to one another.

According to some aspects, an electronic device can include a housing defining an aperture and at least partially defining an internal volume of the electronic device, an electromagnetic radiation emitter and an electromagnetic radiation detector disposed in the internal volume, a unitary optical component disposed in the aperture and separate from the electromagnetic radiation emitter and the electromagnetic radiation detector, the unitary optical component including a first transparent portion overlying one of the electromagnetic radiation emitter or detector, a second transparent portion surrounding the first transparent portion and overlying the other of the electromagnetic radiation emitter or detector, a first opaque portion extending a thickness of the unitary optical component disposed between the first and second transparent portion, a third transparent portion, a second opaque portion extending the thickness of the unitary optical component disposed between the second transparent portion and the third transparent portion, the first, second, and third transparent portions and the first and second opaque portions further defining the exterior surface of the electronic device, wherein the first, second, and third transparent portions define a larger portion of the exterior surface than the first and second opaque portions.

In some examples, the electronic device can further include at least one electromagnetic radiation emitter disposed under the third transparent portion. The electromagnetic radiation emitter can be disposed under the second transparent portion and can further include at least one additional electromagnetic radiation emitter disposed under the second transparent portion.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Figure 1:
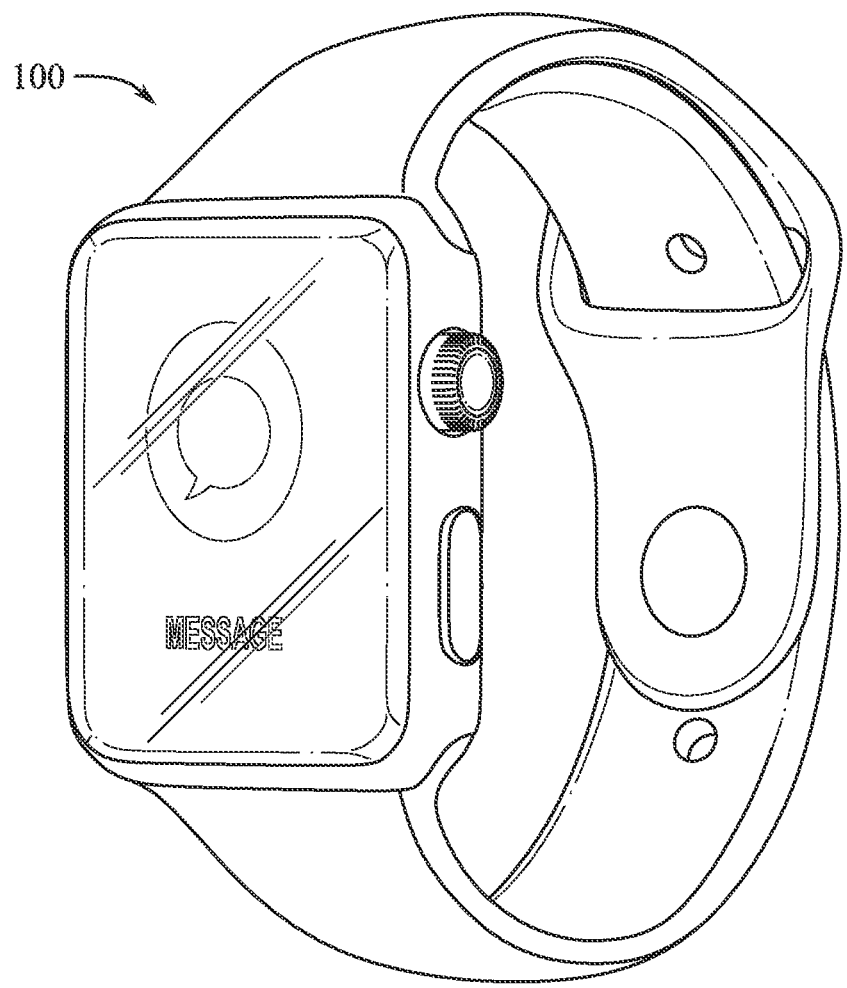
FIG. 1 shows a perspective view of an electronic device.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments, as defined by the appended claims.

One aspect of the present disclosure relates to an electronic device including a housing defining an internal volume, with an electromagnetic radiation emitter and an electromagnetic radiation detector positioned within the internal volume. The housing can define an aperture disposed over the electromagnetic radiation emitter and detector, and a unitary optical component can be disposed in the aperture. The unitary optical component can include a first transparent portion overlying the detector and a second transparent portion overlying the emitter. An opaque portion can be disposed between the first and second transparent portions, and can be bonded, joined, fused, or otherwise connected with the transparent portions. The unitary optical component can define an exterior surface of the electronic device, and the first and second transparent portions and the opaque portion can be flush relative to one another.

Electronic devices increasingly include components that can detect or otherwise receive information based on the ambient environment outside the electronic device. For example, smartphones typically include visible light detectors, such as cameras, that can receive light from the ambient environment which is then processed into an image that is displayed to a user. In addition to components used for detecting properties of the ambient environment, such as light, electronic devices also increasingly include components that can transmit or emit signals or information into the ambient environment. Returning to the example of a smartphone including a visible light detector in the form of a camera, such a device can also include a light emitter in the form a light emitting diode flash component. Such an emitting component can work together with a detector to enhance the amount of information detected from the ambient environment. For example, if the electronic device is in an environment that does not contain enough visible light to produce a significant signal on the light detector of the camera, the flash component can be triggered to emit light to illuminate the ambient environment and allow the detector to receive information appropriate to produce an image.

The packaging of both emitters and detectors in a single electronic device, especially emitters and detectors that can operate in the same range of wavelengths of electromagnetic radiation or light, can sometimes lead to the generation of false signals. In the example of a camera, it is desirable that the camera only detect light, and thus generate a signal, from a desired location in the ambient environment. If the device also includes an emitter in the form of a flash, however, the concurrent use of the emitter and the camera can result in a false signal, if the camera is not optically isolated from the flash. That is, if the flash emits light that travels to the detector through a pathway that is entirely inside the device, the light incident on the detector will not be entirely from the ambient environment, and thus, will not be an accurate depiction of that environment. This condition is also referred to as light leakage or cross-talk. Accordingly, it can be desirable for emitters that emit electromagnetic radiation detectable by a detector and that are internally optically isolated from those detectors.

In addition to camera and flash systems, other electronic device systems can include electromagnetic radiation emitters and detectors. For example, an electronic device can include a vision system designed to assist in providing recognition of an object, or objects. In some instances, the vision system is designed to provide facial recognition of a face of a user of the electronic device. The vision system can include a camera module designed to capture an image, such as a two-dimensional image. The vision system can further include a light emitting module designed to emit several light rays toward the object. The light rays can project a dot pattern onto the object. Further, the light emitting module can emit light in the frequency spectrum of invisible light, such as infrared light (or IR light). The vision system can further include an additional camera module designed to receive at least some of the light rays reflected from the object, and as a result, receive the dot pattern subsequent to the light rays being reflected by the object. The additional camera module can include a light filter designed to filter out light that is not within the frequency spectrum of light emitted from the light emitting module. As an example, the light filter can include an IR light filter designed to block light that is outside the frequency range for IR light. The additional camera module can provide the dot pattern (or a two-dimensional image of the dot pattern) to a processor in the electronic device.

Other exemplary emitter and detector systems that operate in the same or similar ranges of wavelengths of light can include biometric detection systems. These systems can include components that can emit light and project the light onto a user's body, whereupon the emitted light can be at least partially reflected back from the user's body back toward a detector of the device. As the properties of the emitted light are known and controlled by the emitter, the differences between the properties of the light emitted onto the body and the light reflected therefrom and received by the detector can be used to determine a number of biometric or biological properties of the user's body, such as a user's pulse, heart activity, and/or other similar biometric properties.

These and other assemblies or systems including emitters and detectors can include an opaque structural element inside the device that can serve to enclose and optically isolate the emitter components from the detector components. These structural elements typically take the form of walls or chambers that can optically isolate the components in a lateral direction. By their nature, however, the emitters and detectors must have a pathway to emit light to, or receive light from the ambient environment. Accordingly, transparent coverings such as lenses or glasses are typically used to cover the emitters and detectors, and to provide a window to the ambient environment.

Further, it can be desirable for the emitters and detectors of these systems to be disposed relatively near or adjacent to one another, for example, to increase the accuracy or sensitivity of the system. As such, a single lens or transparent cover can be used to provide a light path to the ambient environment for both the emitters and detectors. Even when optically isolated within the housing, such as by an opaque structural element, a light leakage pathway between emitters and detectors can exist through the lens or cover. For example, where a system both emits and receives light with the ambient environment through a single light or cover, some light from the emitter can be internally reflected within a shared lens or cover to reach a detector without first interacting with the ambient environment. As described above, this can result in cross-talk or false signals, and can undesirably impact the performance of the device. Accordingly, a unitary optical component, as described herein, including one or more transparent portions and one or more opaque portions disposed therebetween can act as a lens or cover for the emitters and detectors of a system, without providing any undesirable light pathways, thereby reducing or eliminating any light leakage or cross-talk between emitters and detectors while further optically isolating these components. Furthermore, the unitary optical component serves as a water-resistant barrier, preventing the ingress of moisture to the emitters and detectors.

These and other embodiments are discussed below with reference to FIGS. 1-20B. However, those skilled in the art will readily appreciate that the detailed description given herein with respect to these Figures is for explanatory purposes only, and should not be construed as limiting.

FIG. 1 shows an embodiment of an electronic device 100. The electronic device shown in FIG. 1 is a watch, such as a smartwatch. The smartwatch 100 of FIG. 1 is merely one representative example of a device that can be used in conjunction with the components and methods disclosed herein. The electronic device 100 can correspond to any form of wearable electronic device, a portable media player, a media storage device, a portable digital assistant ("PDA"), a tablet computer, a computer, a mobile communication device, a GPS unit, a remote control device, and other similar electronic devices. The electronic device 100 can be referred to as an electronic device, or a consumer device. Further details of the watch 100 are provided below with reference to FIG. 2.

Figure 2:
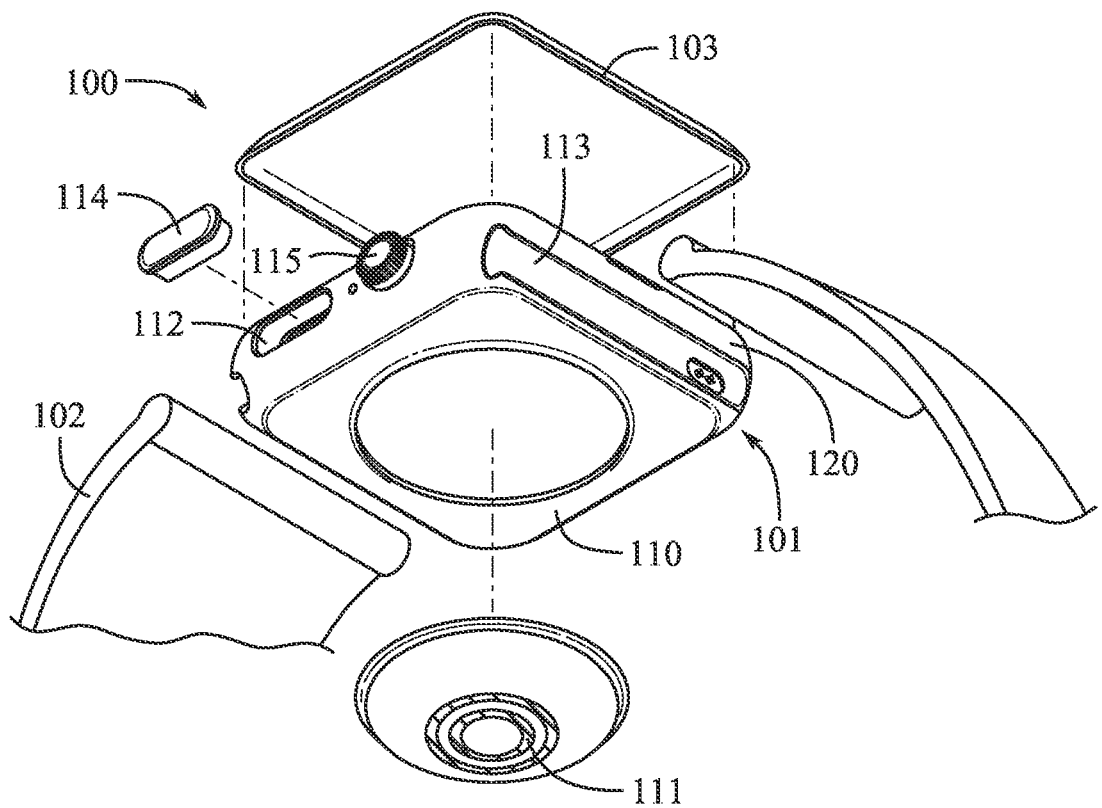
FIG. 2 shows a rear exploded view of the electronic device of FIG. 1.

Referring now to FIG. 2, the electronic device 100 can include a housing 101, and a cover 103 attached to the housing 101. The housing 101 can substantially define at least a portion of an exterior surface of the device 100, and can include a base and sidewalls, such as sidewall 120. The cover 103 can include glass, ceramic, plastic, or any other substantially transparent material, component, or assembly.

The cover 103 can cover or otherwise overlay a display, a camera, a touch sensitive surface such as a touchscreen, or other component of the device 100. The cover 103 can define a front exterior surface of the device 100.

A back cover 110 can also be attached to or form part of the housing 101, for example, opposite the cover 103. The back cover 110 can include ceramic, plastic, metal, or combinations thereof. In some examples, the back cover 110 can include a unitary optical component 111, also referred to as an at least partially electromagnetically transparent component 111. The electromagnetically transparent component 111 can include one or more portions that are transparent to any desired wavelength of electromagnetic radiation, such as visual light, infrared light, radio waves, or combinations thereof, with one or more opaque portions disposed between the electromagnetically transparent portions. In some embodiments, the transparent portions of the unitary optical component 111 can be disposed over one or more electromagnetic radiation emitters and/or detectors, while the opaque portions can inhibit or prevent electromagnetic radiation emitted by an emitter from leaking to a detector along an undesirable pathway. Together, the housing 101, cover 103, and back cover 110 can substantially define an interior volume and an exterior surface of the device 100.

The device 100 can also include internal components, such as a haptic engine, a battery, and a system in package (SiP), including one or more integrated circuits, such as processors, sensors, and memory. The SiP can also include a package. The device 100 can further include one or more electromagnetic radiation emitters and detectors, such as light emitting diodes, cameras, optical detectors, infrared detectors, and other detectors and/or emitters. These emitters and detectors can be associated with one or more systems of the device, such as a camera system, a vision system, and/or a biometric system. The internal components, such as one or more emitters and detectors, can be disposed within an internal volume defined at least partially by the housing 101, and can be affixed to the housing 101 via internal surfaces, attachment features, threaded connectors, studs, posts, or other features, that are formed into, defined by, or otherwise part of the housing 101 and/or the cover 103 or back cover 110. In some embodiments, the attachment features can be formed relatively easily on interior surfaces of the housing 101, for example, by machining.

The housing 101 can be a substantially continuous or unitary component and can include one or more openings 112 to receive components of the electronic device 100, such as a button 114, and/or provide access to an internal portion of the electronic device 100. In some embodiments, the device 100 can include input components such as one or more buttons 114 and/or a crown 115.

The electronic device 100 can further include a strap 102, or other component designed to attach the device 100 to a user or to otherwise provide wearable functionality. In some examples, the strap 102 can be a flexible material that can comfortably allow the device 100 to be retained on a user's body at a desired location. Further, the housing 101 can include a reception feature or features 113 therein that can provide attachment locations for the strap 102. In some embodiments, the strap 102 can be retained on the housing 101 by any desired techniques. For example, the strap 102 can include magnets that are attracted with magnets disposed within the housing 101, or can include retention components that mechanically retain the strap 102 against the housing 101 within the reception feature 113, or combinations thereof. Further details of an example optical component 111 are provided below with reference to FIG. 3.

Figure 3:
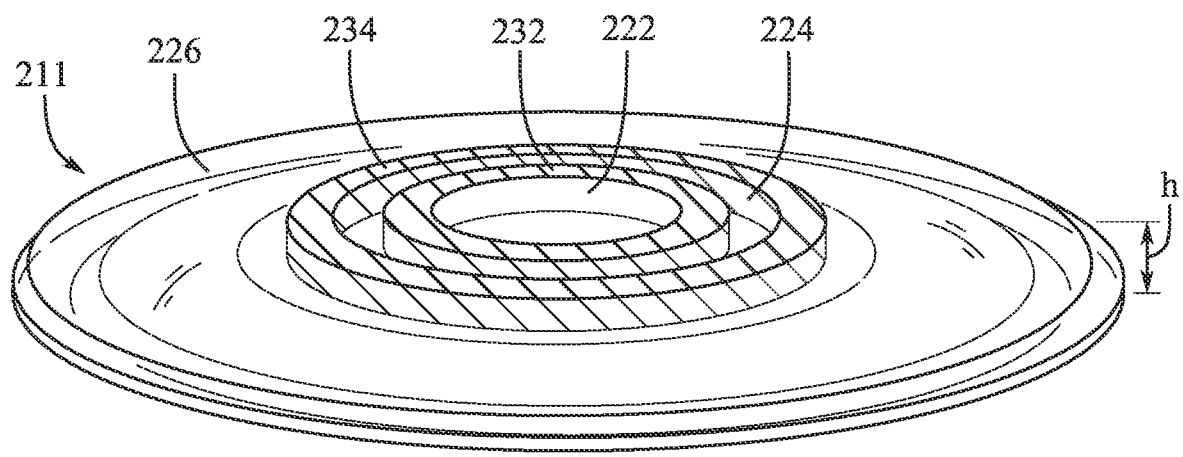
FIG. 3 shows a perspective view of an optical component of an electronic device.

FIG. 3 shows a perspective view of an optical component 211 of an electronic device. The optical component 211 can be similar to, and can include some or all of the features of the optical component 111, described with respect to FIG. 2. As can be seen in FIG. 3, the component 211 can include a first transparent portion 222, a second transparent portion 224, and a third transparent portion 226. In some embodiments, and as illustrated, the second transparent portion 224 can surround the first transparent portion 222 while the third transparent portion 226 can surround both the first and second transparent portions 222, 224. FIG. 3 illustrates just one particular exemplary arrangement of the transparent portions 222, 224, 226. The component 211 can include transparent portions in any number and configuration, as described further herein.

Continuing with FIG. 3, a first opaque portion 232 can be disposed between the first and second transparent portions 222, 224, and a second opaque portion 234 can be disposed between the second and third transparent portions 232, 234. In this embodiment, the opaque portions 232, 234 can entirely surround the perimeter of the respective adjacent transparent portions 222, 224, although in some other examples, one or more opaque portions may not entirely surround a transparent portion. In some examples, the surfaces of the transparent portions 222, 224, 226 and the opaque portions 232, 234 can be level, flush, or in line with one another and can collectively define a surface of the component 211, and can at least partially define the exterior surface of an electronic device, such as device 100. The term "flush" means to be approximately even or level at a surface or within generally the same plane. A "flush" surface can include two or more contiguous surfaces. In some examples, a flush surface can have an average surface roughness ($R_a$) of less than 10 microns, less than 5 microns, less than 1 micron, less than 0.75 microns, less than 0.5 microns, less than 0.25 microns, or less than 0.1 microns or smaller. In some examples, the opaque portions 232, 234 can extend an entire thickness or height "h" of the component 211. In these examples, the opaque portions 232, 234 can prevent electromagnetic radiation, such as visible or infrared light, from being internally reflected in the component 211 from one transparent portion to another transparent portion.

The transparent portions 222, 224, 226, and the opaque portions 232, 234 can be formed from, or can include, substantially any material having the desired levels of transmissivity or opaqueness in any desired range of electromagnetic radiation. For example, the transparent portions 222, 224, 226 can be formed from, or can include, a material that is transparent to electromagnetic radiation in the visible light spectrum, to infrared light, to ultraviolet light, to radio waves, or to any other desired range of wavelengths of light. Further, the transparent portions 222, 224, 226 need not be completely transparent to the desired range or ranges of wavelengths of light. For example, the transparent portions 222, 224, 226 can be 90% transparent, 80% transparent, 70% transparent, 50% transparent, 25% transparent, or even lower for certain applications.

In some embodiments, one or more transparent portions 222, 224, 226 can be formed from, or can include, any desired material, such as ceramics or polymeric materials. In some examples, the one or more transparent portions 222, 224, 226 can include ceramic materials such as glass, sapphire, zirconia, spinel and/or other ceramic materials transparent to a desired range of wavelengths of light. In some examples, the one or more transparent portions 222, 224, 226 can be formed from polymeric materials, such as polycarbonate, acrylics, polyvinyl chloride, polyethylene terephthalate, and/or other polymeric materials transparent to a desired range of wavelengths of light. In some examples, one or more transparent portions 222, 224, 226 can include a ceramic material and one or more other transparent portions 222, 224, 226 can include a polymeric material.

The opaque portions 232, 234 can include or be formed from any material that is substantially opaque to a desired range of wavelengths of light, such as ceramic or polymeric materials. In some embodiments, one or more opaque portions 232, 234 can be formed from or can include any desired material, such as ceramics or polymeric materials. In some examples, the opaque portions 232, 234 can include the same or a similar material as one or more of the transparent portions 222, 224, 226. In some examples, the opaque portions 232, 234 can be formed from the same or a similar material as one or more of the transparent portions 222, 224, 226 and can further include dyes, additives, or pigments that can block or absorb light in a desired range of wavelengths.

The transparent portions 222, 224, 226 and the opaque portions 232, 234 can be joined together by a desired technique to a form a substantially unitary body or component 211. The term "unitary" means to be an approximately singular or solid body. A "unitary" component can include two or more parts or portions that are joined, bonded, fused, or otherwise held together as a single component or piece. For example, an opaque portion 232 can be joined to a transparent portion 222 with an adhesive or by directly fusing the materials of each portions 222, 232 together as described herein. Other methods for bonding, joining, or integrally forming one or more portions can be used in any desired combination. In some embodiments, a surface of the component 211, for example, the surface at least partially defining an exterior surface of an electronic device, can have a larger surface area of transparent material than opaque material. That is, the transparent portions 222, 224, 226 can define a larger surface area of the component 211 than the opaque portions 232, 234. In some other examples, however, the surface of the component 211 at least partially defining an exterior surface of an electronic device can have a larger surface area of opaque material than transparent material.

The electronic device component 211 can include two or more transparent portions and at least one opaque portion disposed therebetween in any number of configurations, as described herein. The process for forming such a unitary component can include any combination of joining, bonding, co-extruding, drawing, molding, or fusing the portions together, as described herein. The unitary component can include a flush exterior surface defined by the opaque and transparent components, and the opaque portion can prevent or inhibit internally reflected light from passing between transparent portions of the component. Various examples of unitary components including opaque and transparent portions are described herein, and processes for forming the same are described below with reference to FIGS. 4-6.

Figure 4:
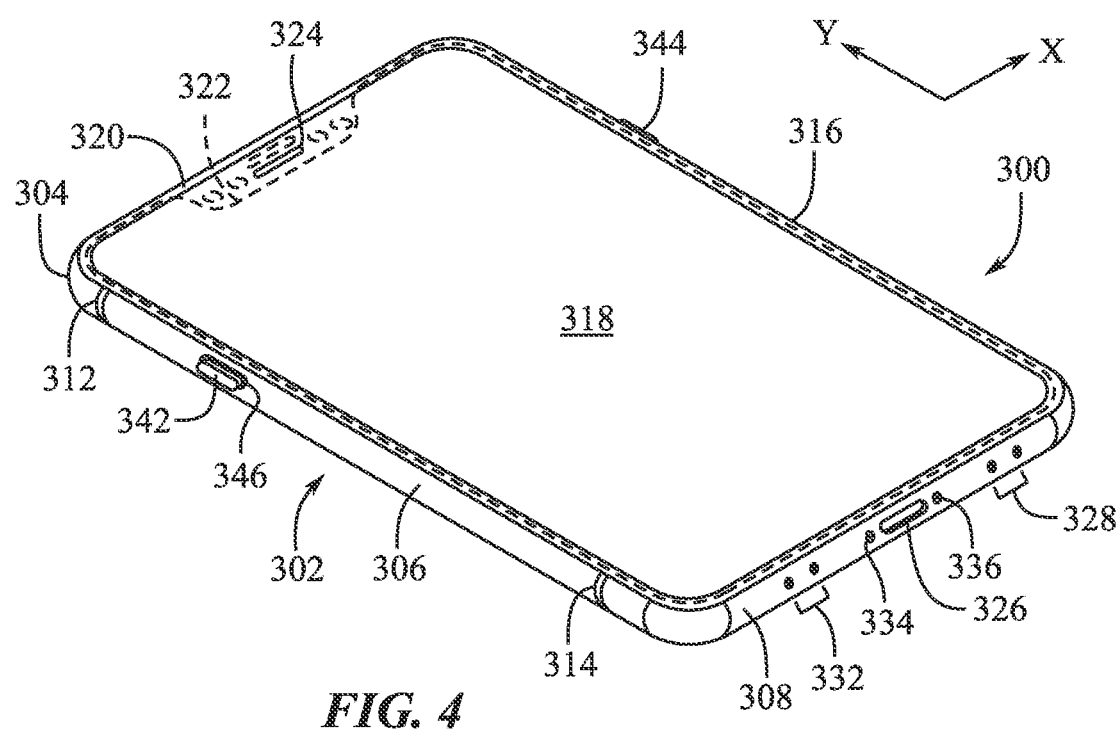
FIG. 4 shows a front perspective front view of an electronic device.

FIG. 4 illustrates a perspective view of an example of an electronic device 300. The electronic device 300 shown in FIG. 4 is a mobile wireless communication device, such as a smartphone. The smartphone of FIG. 4 is merely one representative example of a device that can be used in conjunction with the systems and methods disclosed herein. Electronic device 300 can correspond to any form of wearable electronic device, a portable media player, a media storage device, a portable digital assistant ("PDA"), a tablet computer, a computer, a mobile communication device, a GPS unit, a remote-control device, or any other electronic device. The electronic device 300 can be referred to as an electronic device, or a consumer device.

The electronic device 300 can have a housing that includes a frame or a band 302 that defines an outer perimeter and a portion of the exterior surface of the electronic device 300. The band 302, or portions thereof, can be joined to one or more other components of the device as described herein. In some examples, the band 302 can include several sidewall components, such as a first sidewall component 304, a second sidewall component 306, a third sidewall component 308 (opposite the first sidewall component 304), and a fourth sidewall component (not shown in FIG. 4). The sidewall components can be joined, for example, at multiple locations, to one or more other components of the device, as described herein.

In some instances, some of the sidewall components form part of an antenna assembly (not shown in FIG. 4). As a result, a non-metal material or materials can separate the sidewall components of the band 302 from each other, in order to electrically isolate the sidewall components. For example, a first separating material 312 separates the first sidewall component 304 from the second sidewall component 306, and a second separating material 314 separates the second sidewall component 306 from the third sidewall component 308. The aforementioned materials can include an electrically inert or insulating material(s), such as plastics and/or resin, as non-limiting examples. Further, as described herein, one or more of the sidewall components can be electrically connected to internal components of the electronic device, such as a support plate, as described herein. In some examples, these electrical connections can be achieved by joining a sidewall component to an internal component, for example, as part of the antenna assembly.

The electronic device 300 can further include a display assembly 316 (shown as a dotted line) that is covered by a protective cover 318. The display assembly 316 can include multiple layers (discussed below), with each layer providing a unique function. The display assembly 316 can be partially covered by a border or a frame that extends along an outer edge of the protective cover 318 and partially covers an outer edge of the display assembly 316. The border can be positioned to hide or obscure any electrical and/or mechanical connections between the layers of the display assembly 316 and flexible circuit connectors. Also, the border can include a uniform thickness. For example, the border can include a thickness that generally does not change in the X- and Y-dimensions.

Also, as shown in FIG. 4, the display assembly 316 can include a notch 322, representing an absence of the display assembly 316. The notch 322 can allow for a vision system that provides the electronic device 300 with information for object recognition, such as facial recognition. In this regard, the electronic device 300 can include a masking layer with openings (shown as dotted lines) designed to hide or obscure the vision system, while the openings allow the vision system to provide object recognition information. The protective cover 318 can be formed from a transparent material, such as glass, plastic, sapphire, or the like. In this regard, the protective cover 318 can be referred to as a transparent cover, a transparent protective cover, or a cover glass (even though the protective cover 318 sometimes does not include glass material). Further, in some examples, the protective cover 318 can include some or all of the features of the unitary optical components described herein. In some embodiments, the protective cover 318 can include one or more transparent portions overlying an emitter and/or detector, for example, as associated with the vision system, and can also include one or more opaque portions extending the thickness of the cover 318 and disposed between the transparent portions, as described herein.

As shown in FIG. 4, the protective cover 318 includes an opening 324, which can represent a single opening of the protective cover 318. The opening 324 can allow for transmission of acoustical energy (in the form of audible sound) into the electronic device 300, which can be received by a microphone (not shown in FIG. 4) of the electronic device 300. The opening 324 can also, or alternatively, allow for transmission of acoustical energy (in the form of audible sound) out of the electronic device 300, which can be generated by an audio module (not shown in FIG. 4) of the electronic device 300.

The electronic device 300 can further include a port 326 designed to receive a connector of a cable assembly. The port 326 allows the electronic device 300 to communicate data (send and receive), and also allows the electronic device 300 to receive electrical energy to charge a battery assembly. Accordingly, the port 326 can include terminals that electrically couple to the connector.

Also, the electronic device 300 can include several additional openings. For example, the electronic device 300 can include openings 328 that allow an additional audio module (not shown in FIG. 4) of the electronic device to emit acoustical energy out of the electronic device 300. The electronic device 300 can further include openings 332 that allow an additional microphone of the electronic device to receive acoustical energy. Furthermore, the electronic device 300 can include a first fastener 334 and a second fastener 336 designed to securely engage with a rail that is coupled to the protective cover 318. In this regard, the first fastener 334 and the second fastener 336 are designed to couple the protective cover 318 with the band 302.

The electronic device 300 can include several control inputs designed to facilitate transmission of a command to the electronic device 300. For example, the electronic device 300 can include a first control input 342 and a second control input 344. The aforementioned control inputs can be used to adjust the visual information presented on the display assembly 316 or the volume of acoustical energy output by an audio module, as non-limiting examples. The controls can include one of a switch or a button designed to generate a command or a signal that is received by a processor. The control inputs can at least partially extend through openings in the sidewall components. For example, the second sidewall component 306 can include an opening 346 that receives the first control input 342. Further details regarding the features and structure of an electronic device are provided below, with reference to FIG. 5.

Figure 5:
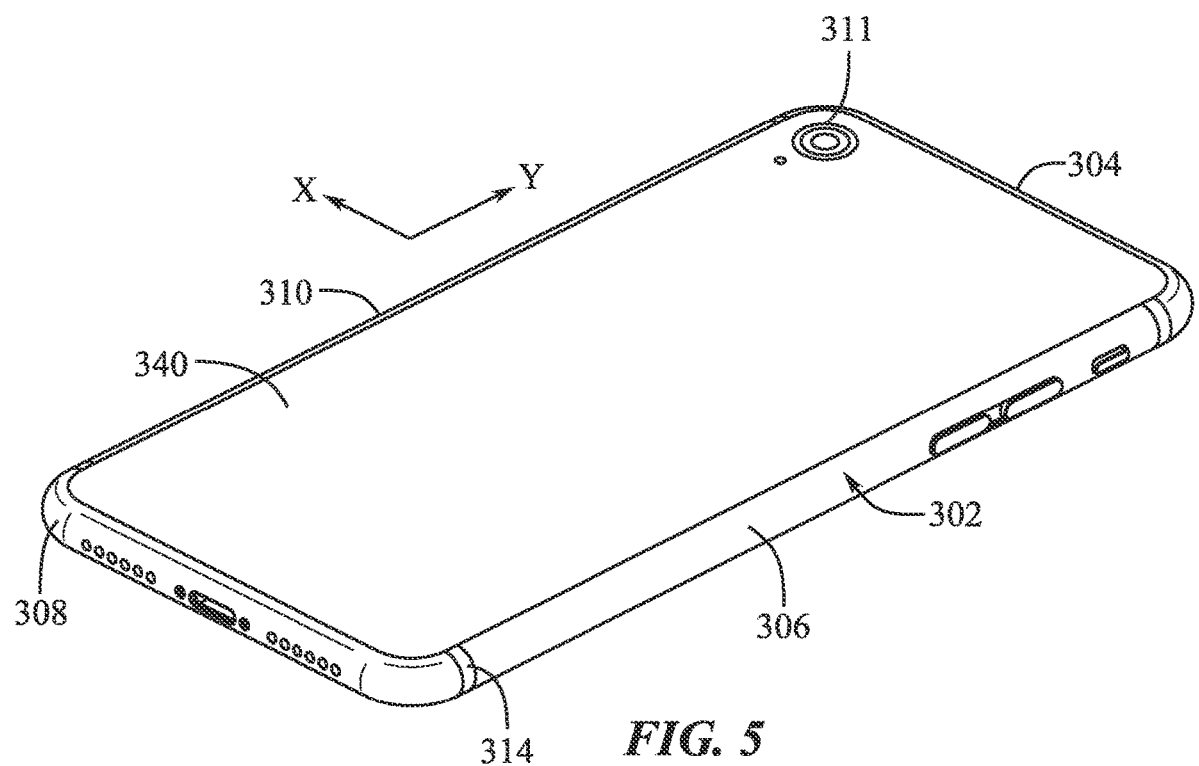
FIG. 5 shows a rear perspective view of the electronic device of FIG. 5

FIG. 5 shows a rear perspective view of the electronic device of FIG. 4. As can be seen, the device 300 can further include a back cover or back protective layer 340 that can cooperate with the band 302 and the protective cover 318 to further define the internal volume and exterior surface of the device 300. The back cover 340 can be formed from any desired material, such as, metals, plastics, ceramics, or composites. In some examples, the back cover 340 can be formed from the same or a similar material as the protective cover 318. In some examples, the back cover 340 can be a conductive transparent material, such as indium titanium oxide or a conductive silica. In some examples, the back cover 340 can define an aperture or orifice that can receive a unitary optical component 311, as described further herein. Additionally, in some examples, the back cover 340 itself can include some or all of the features of the unitary optical components described herein. For example, the back cover 340 can include one or more transparent portions overlying an emitter and/or a detector, for example, as associated with a camera system, and can also include one or more opaque portions extending the thickness of the cover 340 and disposed between the transparent portions, as described herein.

Figure 6:
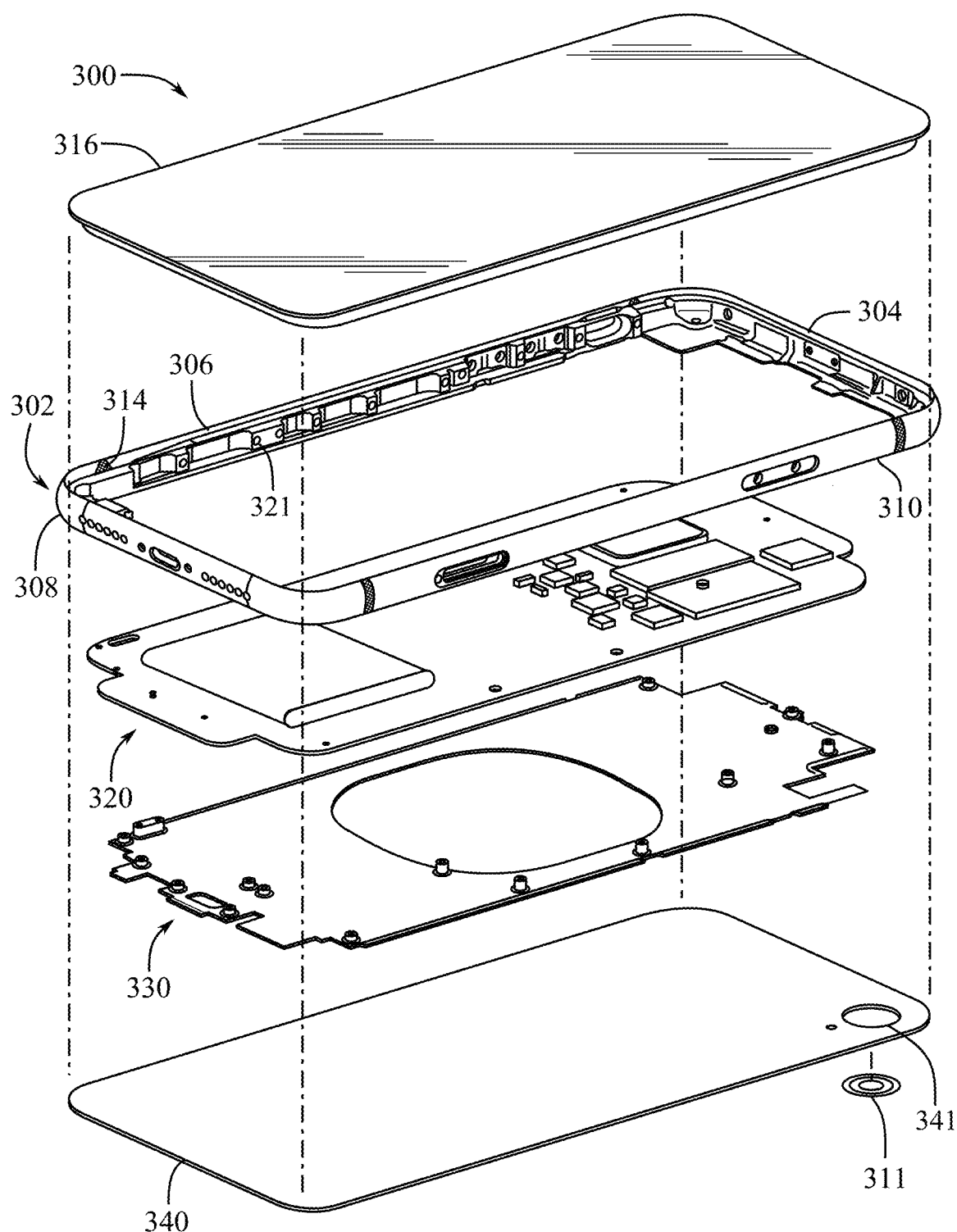
FIG. 6 shows an exploded perspective view of the electronic device of FIG. 5.

FIG. 6 illustrates a perspective exploded view of the electronic device 300. The housing of the device 300, including the band 302, can include one or more features to receive or couple to other components of the device 300. For example, the band 302 can include any number of features such as apertures, cavities, indentations, and other mating features to receive and/or attach to one or more components of the device 300.

The device 300 can include internal components, such as a system in package (SiP), including one or more integrated circuits such as a processors, sensors, and memory. The device 300 can also include a battery housed in the internal volume of the device 300. The device 300 can also include one or more sensors, such as optical or other sensors, that can sense or otherwise detect information regarding the environment exterior to the internal volume of the device 300 as described further herein. Additional components, such as a haptic engine, can also be included in the device 300. The electronic device 300 can also include a display assembly 316, described herein. In some examples, the display assembly 316 can be received by, and/or be attached to, the band 302 by one or more attachment features. In some examples, one or more of these internal components can be mounted to a circuit board 320. The electronic device 300 can further include a support plate 330, also referred to as a back plate or chassis, that can provide structural support for the electronic device 300. The support plate 330 can include a rigid material, such as a metal or metals.

Such components can be disposed within an internal volume defined, at least partially, by the band 302, and can be affixed to the band 302, via internal surfaces, attachment features, threaded connectors, studs, posts, and/or other fixing features, that are formed into, defined by, or otherwise part of the band 302. For example, attachment feature 321 can be formed in the band 302. In some examples, the attachment feature 321 can be formed by a subtractive process, such as machining.

The back cover 340 can also be attached to the band 302, for example, via the one or more attachment features 321, or by any other desired techniques, for example, by an adhesive. The back cover 340 can define at least one aperture 341 that can overlie or be aligned with one or more internal components of the device 300, such as one or more electromagnetic radiation emitters and/or detectors. Such emitters and detectors can be included as part of a vision system, camera system, biometric system, or other systems, as described herein. A unitary optical component 311 can be disposed in the aperture 341, or can be disposed or retained by one or more other components such that the unitary optical component 311 can be disposed over or occlude the aperture 341. The unitary optical component 311 can include at least two transparent portions and at least one opaque portion disposed between the transparent portions, as described herein.

Any number or variety of electronic device components can include two or more transparent portions and at least one opaque portion disposed therebetween, as described herein. The process for forming such a unitary component can include any combination of joining, bonding, co-forming, or fusing the portions together, as described herein. The unitary component can include a flush external surface defined by the opaque and transparent components, and the opaque portion(s) can prevent or inhibit internally reflected light from passing between transparent portions of the component. Various examples of unitary components including opaque and transparent portions as described herein, and processes for forming the same are described below with reference to FIGS. 7-10.

Figure 7:
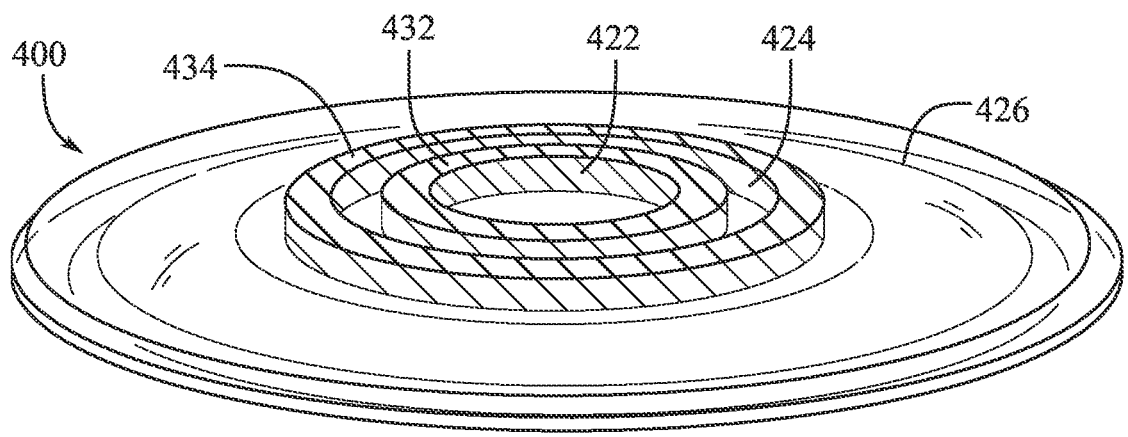
FIG. 7 shows a perspective view of an optical component of an electronic device.

FIG. 7 shows a perspective view of an example unitary optical component 400 that can at least partially define an exterior surface of an electronic device. The unitary component 400 can include some or all of the features of component 211 described herein with respect to FIG. 3, and can be included in an electronic device, such as the devices 100, 300 described herein.

As can be seen in FIG. 7, the component 400 can include a first transparent portion 422, a second transparent portion 424, and a third transparent portion 426. In some embodiments, and as illustrated, the second transparent portion 424 can surround the first transparent portion 422, while the third transparent portion 426 can surround both the first and second transparent portions 422, 424. A first opaque portion 432 can be disposed between the first and second transparent portions 422, 424, and a second opaque portion 434 can be disposed between the second and third transparent portions 422, 424. In this embodiment, the opaque portions 432, 434 can surround the entire perimeter of the respective adjacent transparent portions 422, 424. Although, in some other examples, one or more opaque portions can only partially surround a transparent portion. In some examples, the external surfaces of the transparent portions 422, 424, 426 and the opaque portions 432, 434 can be level, flush, or in line with one another, and can collectively define a surface of the component 400 that can at least partially define the exterior surface of an electronic device including the component 400. Further details of the component 400 are provided below with reference to FIG. 8.

Figure 8:
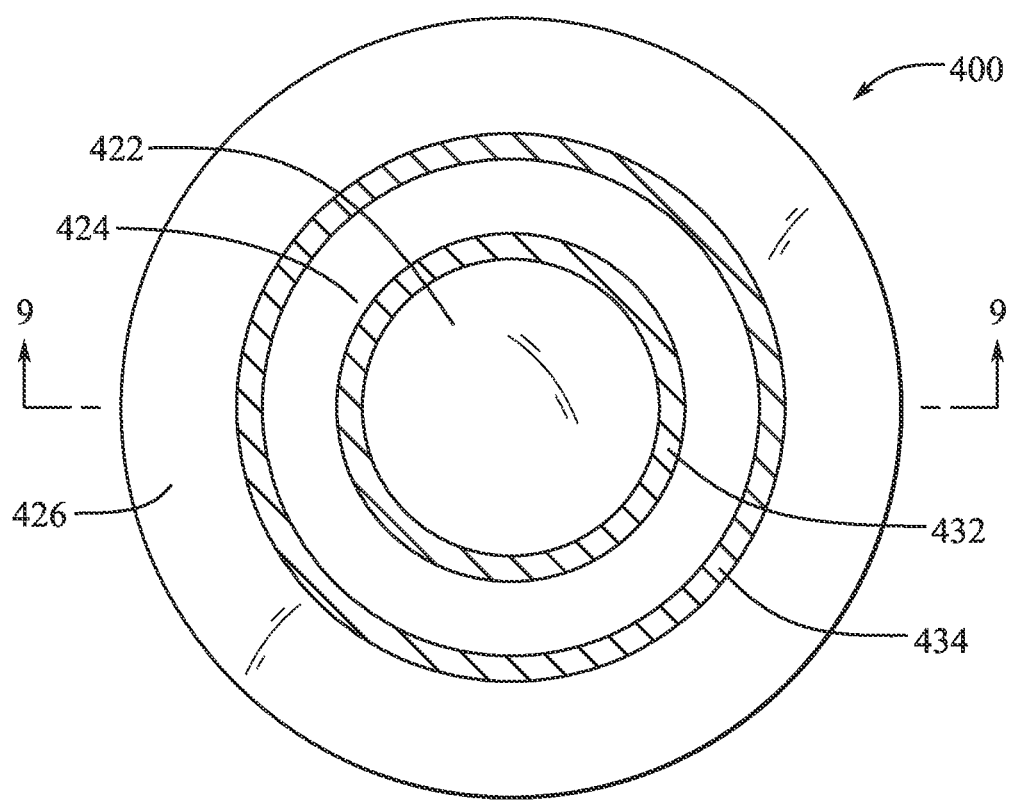
FIG. 8 shows a top view of the optical component of FIG. 7.

FIG. 8 shows a top view of the unitary optical component 400 of FIG. 7. As shown in this embodiment, the unitary component 400 can be substantially circular or have a substantially circular perimeter. Further, the transparent portions 422, 424, 426 and the opaque portions 432, 434 can also have a substantially circular or rounded perimeter, for example, corresponding to the shape of the perimeter of the component 400. In some other embodiments, the component 400 can have any desired perimeter shape, such as a rectangular, a triangular, or an irregularly shaped perimeter. In some examples, the perimeter shape of one or more of the transparent portions 422, 424, 426 and the opaque portions 432, 434 may not match or correspond to the perimeter shape of the component 400. Alternatively, the external geometries of the transparent portions 422, 424, 426 and the opaque portions 432, 434 can differ from one another.

In some embodiments, and as shown in FIG. 8, a transparent portion 422, 424, 426 can have a greater width than an adjacent opaque portion 432, 434. For example, the transparent portion 424 can be wider than the opaque portion 432 and/or the opaque portion 434. Additionally, each opaque portion 432, 434 can be a substantially continuous or solid piece of material. In some examples, however, the opaque portions 432, 434 can be formed from or can include multiple portions that can be joined, bonded, co-formed, or fused together during a formation process to form the unitary component 400.

Owing at least partially to the fact that the opaque portions 432, 434 can be narrower than the adjacent transparent portions 422, 424, 426 in some embodiments, as can be seen in FIG. 8, the transparent portions 422, 424, 426 can include a larger area of the surface of the component 400 than the opaque portions 432, 434. In some examples, such a configuration can allow for desired amounts of electromagnetic radiation to be transmitted through the transparent portions 422, 424, 426 of the component 400, while still preventing electromagnetic radiation from being internally reflected or leaking between the transparent portions 422, 424, 426. Further details of the unitary component are provided below with reference to FIG. 9.

Figure 9:
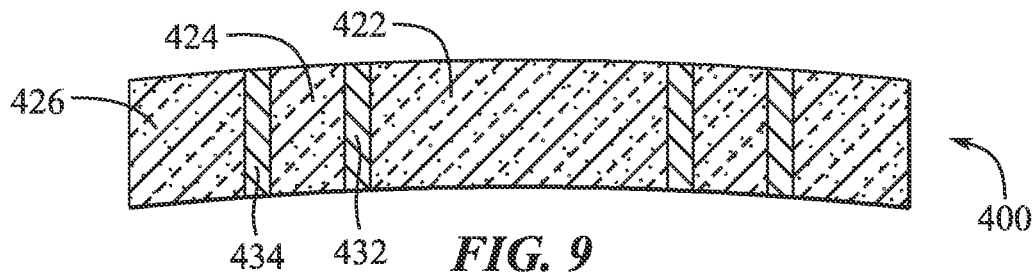
FIG. 9 shows a cross-sectional side view of the optical component of FIG. 7.

FIG. 9 shows a side cross-sectional view of the unitary optical component 400 of FIG. 7 taken through the center of the component 400. In some embodiments, the surface of the component 400 that can at least partially define an exterior surface of an electronic device, for example, the top surface of the component 400 as illustrated in FIG. 9, can have a substantially uniform, regular, continuous, or uninterrupted profile, such as the curved profile shown in FIG. 9. That is, the surface may smoothly or seamlessly transition between those areas of the surface defined by transparent portions 422, 424, 426 and those areas of the surface defined by the opaque portions 432, 434. In some embodiments, as described herein, the transparent portions 422, 424, 426 and the opaque portions 432, 434 can be co-finished.

As can be seen in FIG. 9, the opaque portions 432, 434 extend through the entire thickness of the component 400. That is, the transparent portions 422, 424, 426 are not laterally connected to each other at the location of the opaque portions 432, 434. In this way, any light that is inadvertently internally reflected in a transparent portion, for example, transparent portion 424, cannot pass into another transparent portion, such as portions 422, 426 without exiting the transparent portion 424 through a top or a bottom surface thereof and then reentering the other transparent portion 422, 426 through a top or a bottom surface thereof. That is, in some examples, the opaque portions 432, 434 can completely block or inhibit any internal reflection pathways between the transparent portions 422, 424, 426, thereby preventing or inhibiting cross-talk and reducing detector noise, as described herein. Further details of the construction of the unitary optical component 400 are provided below with reference to FIG. 10.

Figure 10:
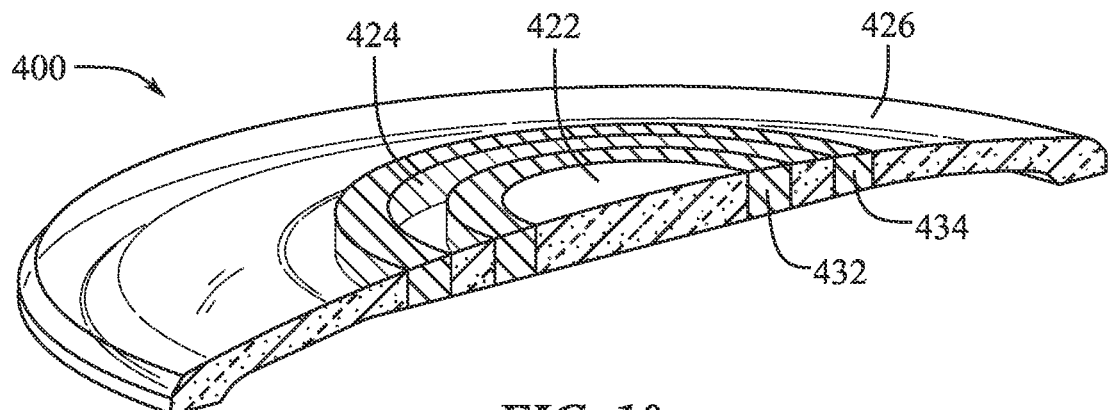
FIG. 10 shows a perspective cross-sectional view of the optical component of FIG. 7.

FIG. 10 shows a perspective cross-sectional view of the unitary optical component 400 of FIG. 7. As shown in FIG. 10, the transparent portions 422, 424, 426 and the opaque portions 432, 434 together define a single continuous surface profile of the component 400. Further, the component 400 itself can have any desired shape or profile. For example, as illustrated in FIG. 10, the unitary optical component 400 can have a concave or lens shaped profile that is defined by the exterior surfaces of the transparent portions 422, 424, 426 and the opaque portions 432, 434. In some embodiments, the unitary optical component 400 can have any desired shape or profile, such as a curved shape, a flat or planar shape, a shape including one or more non-planar features defined, at least in part, by the transparent portions 422, 424, 426 and the opaque portions 432, 434.

Any number or variety of electronic device components can include two or more transparent portions and at least one opaque portion disposed therebetween as described herein. The process for forming such a unitary component can include any combination of joining, bonding, co-extruding, pull-truding, molding, or fusing the portions together, as described herein. The unitary component can include a flush surface defined by the opaque and transparent components, and the opaque portion can prevent or inhibit internally reflected light from passing between transparent portions of the component. Various examples of unitary components including opaque and transparent portions as described herein, and processes for forming the same are described below with reference to FIGS. 11A-12.

Figure 11A:
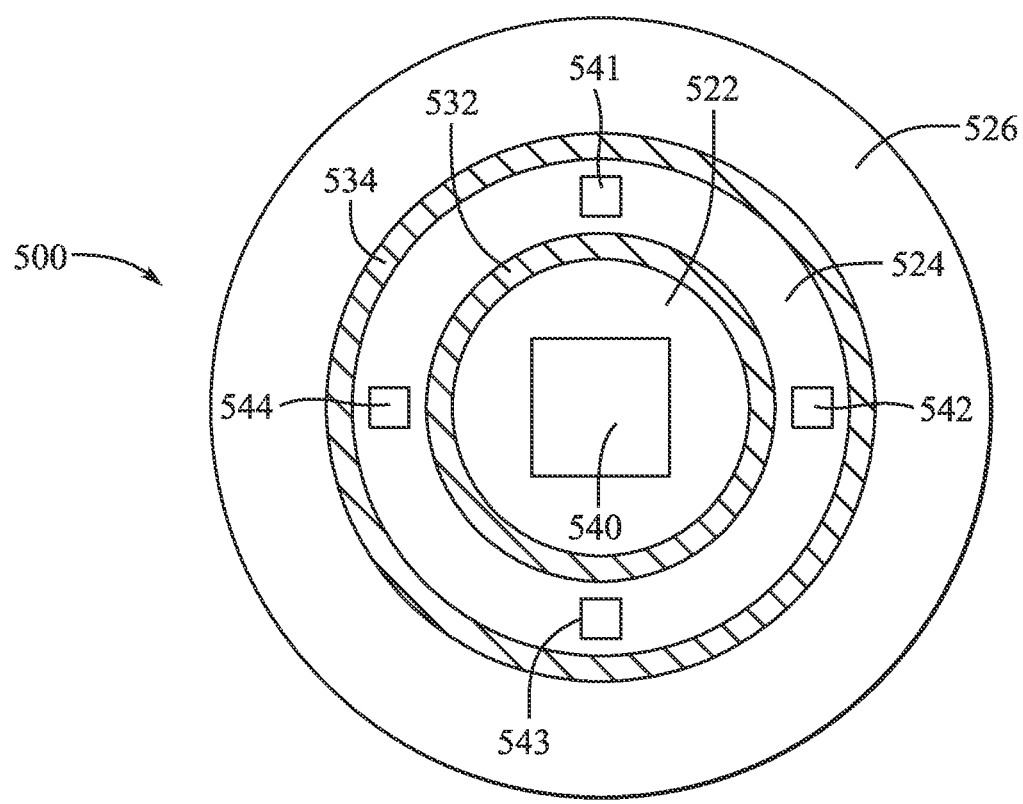
FIG. 11A shows a top view of components of an electronic device.

FIG. 11A shows a top view of a unitary optical component 500 of an electronic device, as described herein, overlying an electromagnetic radiation detector 540 and electromagnetic radiation emitters 541, 542, 543, 544. In some embodiments, the unitary optical component 500 can be similar to, or the same as, and include some or all of the features of the unitary optical components 111, 211, 311, 400 described herein. In the present example, the unitary optical component 500 can at least partially define an exterior surface and an internal volume of an electronic device. The electromagnetic radiation detector 540 and electromagnetic radiation emitters 541, 542, 543, 544 can be disposed in the internal volume of the device underlying the unitary optical component 500, as described herein.

As can be seen in FIG. 11A, the electromagnetic radiation detector 540 can be disposed under or underlie a first transparent portion 522 of the unitary optical component 500. Accordingly, the electromagnetic radiation detector 540 can detect a desired range of wavelengths of electromagnetic radiation that enter the internal volume through the first transparent portion 522. As described herein, a first opaque portion 532 can surround the first transparent portion 522 and can prevent or inhibit light that has entered or is incident on other portions of the unitary optical component 500 from reaching the detector 540 without first passing through an exterior surface of the first transparent portion 522. In some examples, the electromagnetic radiation detector 540 can detect visible light, infrared light, ultraviolet light, microwaves, and/or any other desired range or ranges of wavelengths of light.

An electromagnetic radiation emitter 541 can be disposed under a second transparent portion 524 of the unitary component 500, with the first opaque portion 532 disposed between the first transparent portion 522 and the second transparent portion 524. In this particular example, the second transparent portion 524 can surround the first opaque portion 532 and the first transparent portion 522, although other configurations are expressly contemplated. Accordingly, in order for electromagnetic radiation emitted from the emitter 541 to reach the detector 540, the electromagnetic radiation must exit the external surface of the second transparent portion 524, whereupon it can reflect off of or otherwise interact with the environment outside the electronic device, before reentering the internal volume through the external surface of the first transparent portion 522. This elimination or reduction of total internal reflection pathways between transparent portions 522, 524 of the unitary component 500 can allow for a significant reduction in undesirable cross-talk between the emitter 541 and the detector 540, as described herein.

In some embodiments, one or more additional electromagnetic radiation emitters 542, 543, 544 can be disposed under the second transparent portion 524. In the present example, the four emitters 541, 542, 543, 544 can all be disposed under a single second transparent portion 524, although as described herein, in some other examples, each emitter 541, 542, 543, 544 can be disposed under separate or divided second portions. In some examples, the emitters 541, 542, 543, 544 can be symmetrically spaced or disposed under the second portion 524, however, any configuration of emitters 541, 542, 543, 544 is contemplated. In some embodiments, an electromagnetic radiation emitter 541, 542, 543, 544 can emit electromagnetic radiation in a desired range of wavelengths at one or more desired intensities, for one or more desired durations. In some examples, an emitter 541, 542, 543, 544 can emit visible light, infrared light, ultraviolet light, and/or any other range or ranges of electromagnetic radiation. In some embodiments, one or more of the emitters 541, 542, 543, 544 can be a semiconductor light source, such as a light emitting diode, a laser, or any other desired component capable of emitting electromagnetic radiation.

The unitary optical component 500 can further include a third transparent portion 526 that can surround the second transparent portion 524. A second opaque portion 534 can be disposed between the second and third transparent portions 524, 526, and can serve the same or a similar function as the first opaque portion 532. That is, the second opaque portion 534 can serve to optically isolate the volume under the adjacent transparent portions 524, 526 by preventing or inhibiting any total internal reflection pathways therebetween through the unitary optical component 500. As with the first opaque portion 532, the second opaque portion 534 can prevent light emitted by the emitters 541, 542, 543, 544 from entering the volume under the third transparent portion 526 without first exiting through the external surface of the second transparent portion 524 and reentering the third transparent portion 526.

Figure 11B:
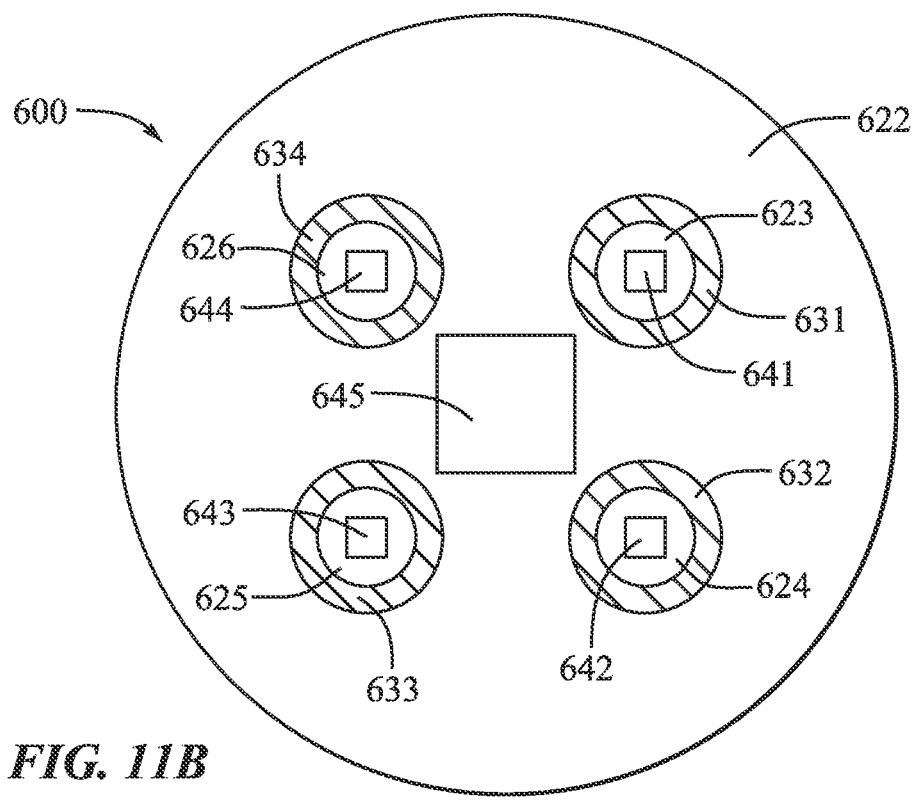
FIG. 11B shows a top view of components of an electronic device.

FIG. 11B shows another embodiment of a unitary optical component 600 of an electronic device, as described herein, overlying an electromagnetic radiation detector 645 and electromagnetic radiation emitters 641, 642, 643, 644. In some embodiments, the unitary optical component 600 can be similar to, or the same as, and can include some or all of the features of the unitary optical components 111, 211, 311, 400, 500 described herein. In the present example, the unitary optical component 600 can at least partially define an exterior surface and an internal volume of an electronic device. The electromagnetic radiation detector 645 and electromagnetic radiation emitters 641, 642, 643, 644 can be disposed in the internal volume of the device underlying the unitary optical component 600, as described herein.

The unitary optical component 600 can include a first transparent portion 622 overlying the detector 645. The unitary optical component can further include a number of opaque portions 631, 632, 633, 634 that can be disposed between the first transparent portion 622 and the second transparent portions 623, 624, 625, 626 overlying the emitters 641, 642, 643, 644. Thus, in some examples, the first transparent portion 622 can surround one or more separate or discrete second transparent portions 623, 624, 625, 626 that can, for example, overlie one or more emitters 641, 642, 643, 644 and can be surrounded by respective opaque portions 631, 632, 633, 634.

Figure 11C:
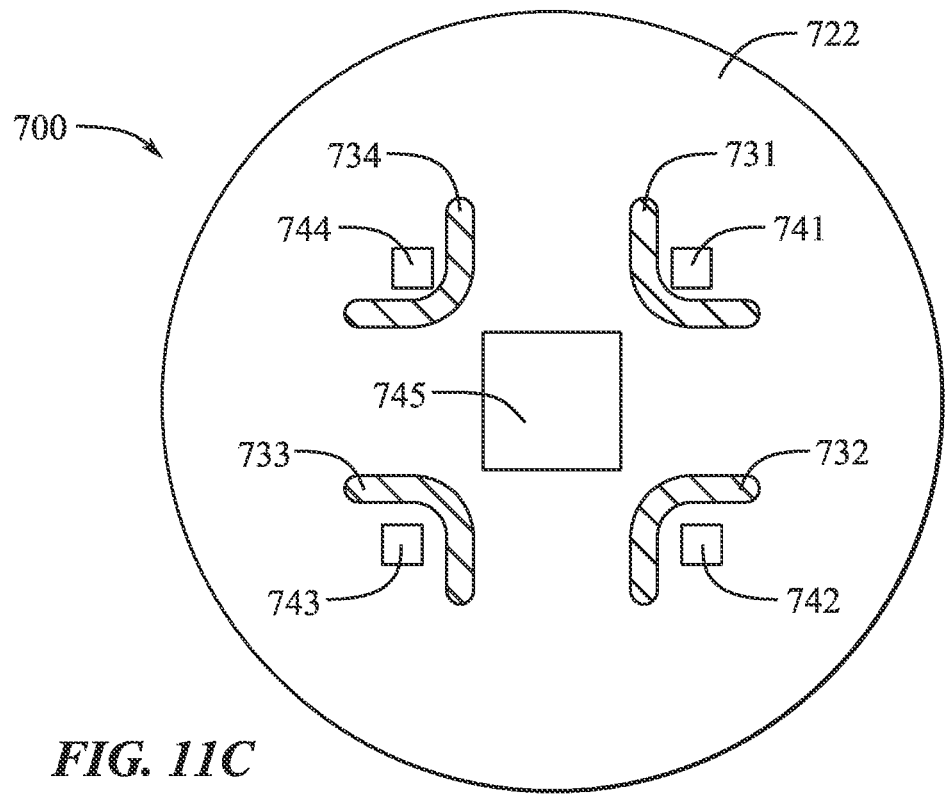
FIG. 11C shows a top view of components of an electronic device.

FIG. 11C shows another embodiment of a unitary optical component 700 of an electronic device, as described herein, overlying an electromagnetic radiation detector 745 and electromagnetic radiation emitters 741, 742, 743, 744. In some embodiments, the unitary optical component 700 can be similar to, or the same as, and can include some or all of the features of the unitary optical components 111, 211, 311, 400, 500, 600 described herein. In the present example, the unitary optical component 700 can at least partially define an exterior surface and an internal volume of an electronic device. The electromagnetic radiation detector 745 and the electromagnetic radiation emitters 741, 742, 743, 744 can be disposed in the internal volume of the device underlying the unitary optical component 700, as described herein.

As with the example illustrated in FIG. 11B, the unitary optical component 700 can include a first transparent portion 722 that overlies an electromagnetic radiation detector 745 that is disposed thereunder. The unitary optical component 700 can further include a number of opaque portions 731, 732, 733, 734 that can be disposed in the first transparent portion 722 between the emitters 741, 742, 743, 744 and the electromagnet radiation detector 745. In some examples, the opaque portions 731, 732, 733, 734 do not entirely surround the transparent portions overlying the emitters 741, 742, 743, 744. That is, in some examples, the opaque portions 731, 732, 733, 734 can be disposed only between the first transparent portion 722 and other transparent portions at select or desired locations, while the first transparent portion 722 can directly abut or be integral with the second or another transparent portion at another location. Accordingly, in some examples, the first transparent portion 722 can be continuous with, joined to, co-formed with, or otherwise in contact with one or more second portions, for example, those portions overlying the emitters 741, 742, 743, 744. The opaque portions 731, 732, 733, 734 can be disposed at locations designed to minimize cross-talk or light-leakage between the emitters 741, 742, 743, 744 and the detector, but not at other locations that may have little or no effect on minimizing cross-talk or light-leakage.

Although certain components are described as electromagnetic radiation emitters and others are described as electromagnetic radiation detectors, it should be understood that either an electromagnetic radiation emitter or detector or both can be provided at any of the locations of these components in any of the embodiments described herein. That is, although component 645 is described as an electromagnetic radiation detector, in some embodiments, the component 645 can be an electromagnetic radiation emitter, or a component that selectively functions as both an emitter and a detector. Further details of the unitary optical component and its structure are provided below with reference to FIG. 12.

Figure 12:
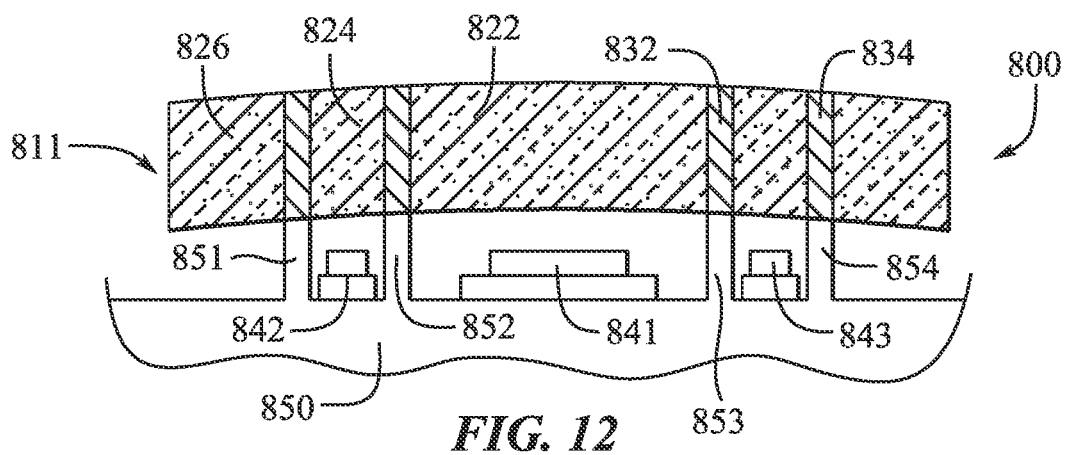
FIG. 12 shows a cross-sectional side view of components of an electronic device.

FIG. 12 shows a cross-sectional view of an electronic device 800 including a unitary optical component 811 that at least partially defines an external surface and an internal volume of the device 800. The device 800 can further include an electromagnetic radiation detector 841 and electromagnetic radiation emitters 842, 843 disposed under the unitary optical component 811 in the internal volume. In some embodiments, the unitary optical component 811 can be similar to, or the same as, and can include some or all of the features of the unitary optical components 111, 211, 311, 400, 500, 600, 700 described herein. In the present example, the unitary optical component 811 can be substantially similar to the unitary optical component 500 illustrated with respect to FIG. 11A.

As can be seen in FIG. 12, the unitary optical component 811 can include a first transparent portion 822 disposed over the detector 841, an annular second transparent portion 824 disposed over the emitters 842, 843, and an annular first opaque portion 832 disposed between the first and second transparent portions 822, 824, and extending the entire thickness of the component 811. A third transparent portion 826 can surround the first and second transparent portions 822, 824, and can be separated therefrom by a second opaque portion 834 that extends the entire thickness of the component 811 to prevent cross-talk or internal reflection pathways between portions, as described herein.

The device 800 can further include an isolation component 850 that is disposed in the internal volume and that, in some examples, can carry or have one or more of the detector 841 and emitters 842, 843 mounted thereon. The isolation component can include opaque or light-blocking protrusions 851, 852, 853, 854 that can encompass, surround, and separate the detector 841 and the emitters 842, 843 in the internal volume of the device 800. Thus, the opaque protrusions 851, 852, 853, 854 can define one or more isolation chambers, with the detector 841 disposed in a first isolation chamber, and the emitters 842, 843 disposed in a second isolation chamber. In some examples, the opaque protrusions 851, 852, 853, 854 can be disposed below, or can underlie, some or all of the opaque portions 832, 834. Thus, in some examples, one or more of the opaque protrusions 851, 852, 853, 854 can have the same or a similar shape as one or more of the opaque portions 832, 834.

In some embodiments, the opaque protrusions 851, 852, 853, 854 can directly abut or contact a lower surface of the unitary optical component 811, for example, a surface at least partially defined by the opaque portions 832, 834. In some examples, the opaque protrusions 851, 852, 853, 854 can be joined, fused, or otherwise bonded to the unitary optical component 811, for example, at the opaque portions 832, 834. In some examples, the opaque protrusions 851, 852, 853, 854 can be bonded to the unitary optical component 811 by an adhesive. Further, in some examples, the adhesive can be an opaque adhesive, such as an adhesive including a light-blocking or light-absorbing dye or other additive. Accordingly, in some embodiments, electromagnetic radiation emitted by the electromagnetic radiation emitters 842, 843 must pass entirely through the second transparent portion 824 in order to exit the isolation chamber or chambers defined, at least partially, by the isolation component 811 because no other pathway from the emitters 842, 843 to the ambient environment of the detector 841 exists.

Any number or variety of electronic device components can include two or more transparent portions and at least one opaque portion disposed therebetween, as described herein. The process for forming such a unitary component can include any combination of joining, bonding, or fusing the portions together, as described herein. The unitary component can include a flush outer surface defined by the opaque and transparent components, and the opaque portion can prevent or inhibit internally reflected light from passing between transparent portions of the component. Various examples of unitary components, including opaque and transparent portions as described herein, and processes for forming the same are described below, with reference to FIGS. 13A-20B.

Figure 13A:
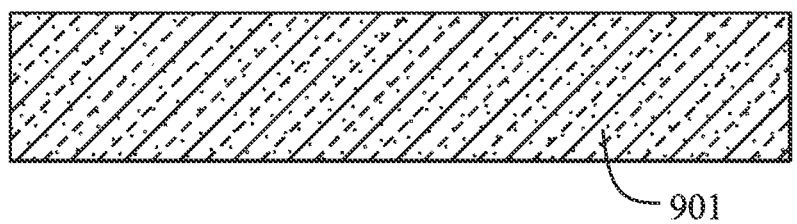
FIG. 13A shows a cross-sectional side view of a component at a stage during a formation process.

FIG. 13A shows a cross-sectional view of a portion of material 901 that can be formed into a unitary optical component, as described herein. In some examples, the portion of material 901 can be transparent to one or more desired ranges of wavelengths of electromagnetic radiation, and can include a ceramic or polymeric material, as described herein. In some examples, the transparent material 901 can be a substantially unitary or continuous portion of material. The material 901 can be any shape or size, but in some examples, the portion of material 901 can have a shape and/or size corresponding to, or approximately, the same as the formed unitary optical component.

Figure 13B:
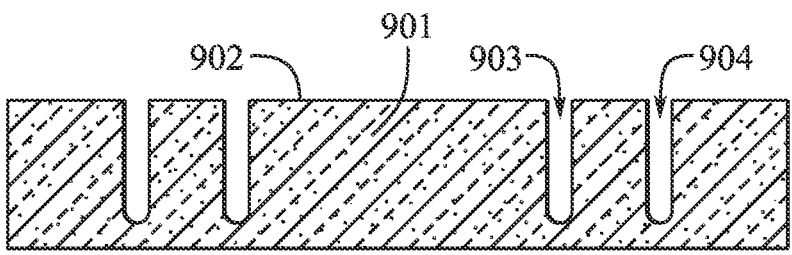
FIG. 13B shows a cross-sectional side view of a component at a stage during a formation process.

As shown in FIG. 13B, one or more trenches, cavities, or recesses 903, 904 can be formed into the material 901. In some examples, the recesses 903, 904 can be formed by a subtractive manufacturing process applied to a surface 902 of the material 901, such as machining, cutting, etching, or any other desired process. In some other examples, material can be added to the surface 902 to define the recesses 903, 904, for example, by an additive process such as 3D printing. In some examples, the recess 903 can have a size, shape, and/or depth corresponding to a desired design of a first opaque portion, and the recess 904 can have a size, shape, and/or depth corresponding to a desired design of a second opaque portion.

Figure 13C:
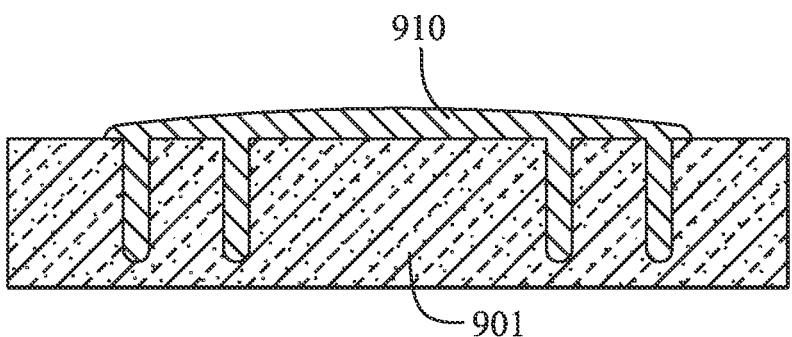
FIG. 13C shows a cross-sectional side view of a component at a stage during a formation process.

As shown in FIG. 13C, subsequent to or concurrent with the formation of the recesses 903, 904, the recesses 903, 904 can be infilled with an opaque material 910. The opaque material 910 can include any opaque material having the desired light-blocking or absorbing properties, as described herein. In some examples where the portion of material 901 can include a polymeric material, the opaque material 910 can also include a polymeric material, for example, a same or similar polymeric material. Thus, in some embodiments, infilling the opaque material 910 into the recesses 903, 904 can include bonding or fusing the opaque material 910 to the transparent material 901 in the recesses 903, 904.

Figure 13D:
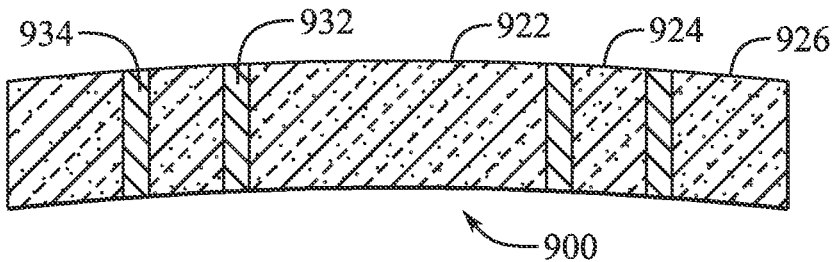
FIG. 13D shows a cross-sectional side view of a formed component.

As shown in FIG. 13D, The transparent material 901 including opaque material 910 filled into the recesses 903, 904 can then be treated to achieve a final desired shape or design of the unitary optical component 900, with the opaque material 910 now defining separate or discrete opaque portions 932, 934 and the transparent material 901 now defining separate or discrete transparent portions 922, 924, 926, as described herein. In some embodiments, the unitary optical component 900 can be similar to, or can be the same as, and can include some or all of the features of the unitary optical components 111, 211, 311, 400, 500, 600, 700, 811 described herein. For example, the component 900 can include a curved or otherwise non-planar surface that can at least partially define an exterior surface of an electronic device, and can also include a curved other otherwise non-planar surface that can at least partially define an internal volume of the electronic device. In some examples, the final shape of the component 900 can be achieved by a subtractive process, such as machining or cutting. In some examples, the final shape of the component 900 can be achieved by a forging or a pressing process. Additional component configurations are detailed below with reference to FIGS. 14A and 14B.

Figure 14A:
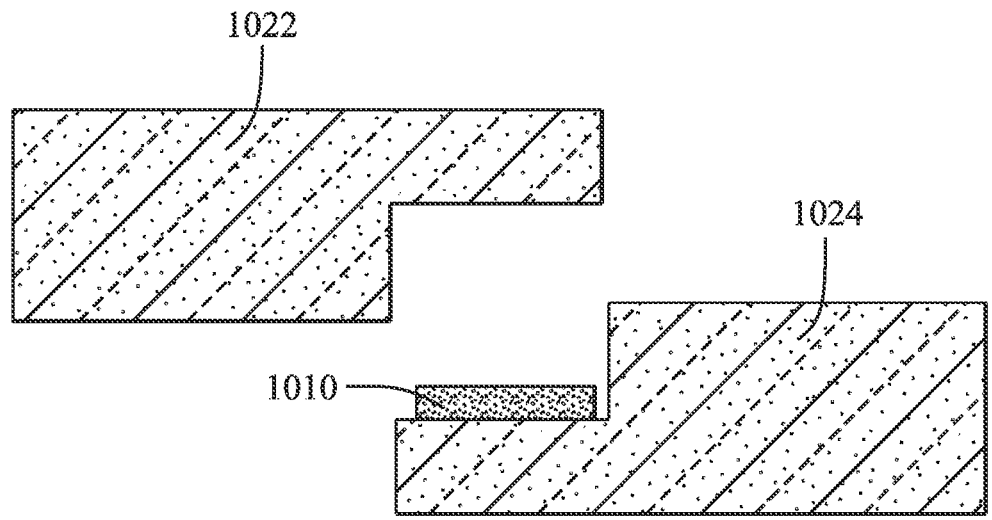
FIG. 14A shows a cross-sectional side view of a component at a stage during a formation process.

FIG. 14A shows a side cross-sectional view of two transparent portions of material 1022, 1024 that can be combined, bonded, or joined to form a unitary optical component, as described herein. In some examples, the first transparent portion 1022 can have a shape corresponding to, or similar to, a first transparent portion of the final formed unitary optical component. Similarly, the second transparent portion 1024 can have a shape corresponding to, or similar to, a second transparent portion of the final formed unitary optical component. Each of the first or second transparent portions 1022, 1024 can be formed by any desired process, such as an additive or subtractive manufacturing process. In some examples, each portion 1022, 1024 can be cut or formed from a single or unitary piece of transparent material. An adhesive or other opaque material 1010 can be added to either or both of the transparent portions 1022, 1024 to bond or join the portions 1022, 1024 together. In some examples, the adhesive 1010 can be an opaque adhesive, such as an adhesive including a light-blocking or light-absorbing dye or other additive.

Figure 14B:
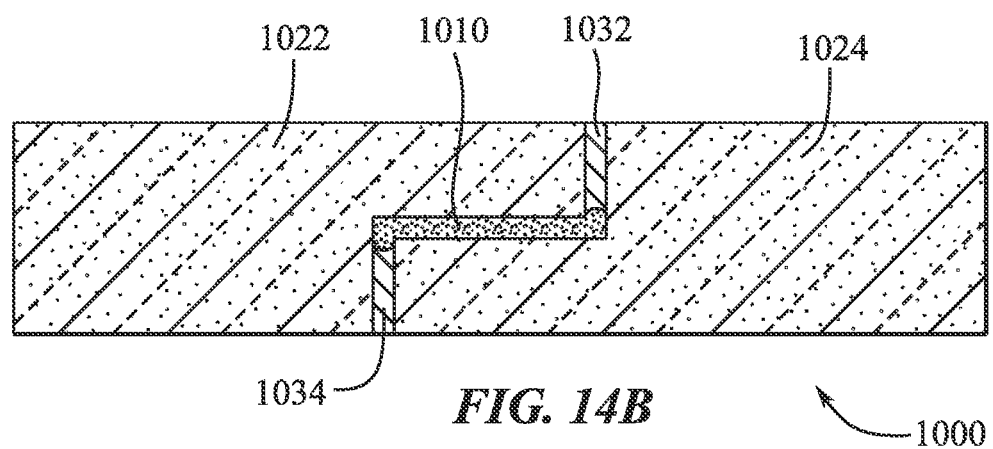
FIG. 14B shows a cross-sectional side view of a formed component.

As shown in FIG. 14B, the transparent portions 1022, 1024 can be adhered together by the adhesive 1010 in a desired configuration to form the unitary optical component 1000. In some embodiments, the unitary optical component 1000 can be similar to, or the same as, and can include some or all of the features of the unitary optical components 111, 211, 311, 400, 500, 600, 700, 811, 900 described herein. In some examples, the transparent portions 1022, 1024 can be joined such that one or more surfaces of each portion 1022, 1024 are offset from one another to define one or more gaps. These gaps can then be infilled with opaque material to form opaque portions such as portions 1032, 1034. The material used to form the opaque portions 1032, 1034 can be any desired opaque material, as described herein, such as an opaque ceramic or polymeric material that is the same as or similar to the material of the transparent portions 1022, 1024. In some examples, the opaque portions 1032, 1034 can further bond, join, or fuse with the transparent portions 1022, 1024, thereby forming the unitary optical component 1000.

Accordingly, the opaque portions 1032, 1034 and the adhesive 1010 can collectively define a single opaque portion that can include some or all of the features of any of the opaque portions of the unitary optical components described herein, and that can optically isolate the first transparent portion 1022 from the second transparent portion 1024 in the unitary optical component 1000. As can be seen in FIG. 14B, the opaque portion defined by the opaque portions 1032, 1034 and the adhesive 1010 can have one or more non-planar sidewalls. Further, the opaque portion 1032 can be laterally offset from the opaque portion 1034. This configuration can, for example, provide the opaque portion defined by the opaque portions 1032, 1034 and the adhesive 1010 with an effective width equivalent to the offset between the opaque portions 1032, 1034 while using less material than if the opaque portion were define by a single piece of material having a width equal to the offset, thus reducing manufacturing and material costs. Additional configurations of the component are detailed below with reference to FIGS. 15A-15B.

Figure 15A:
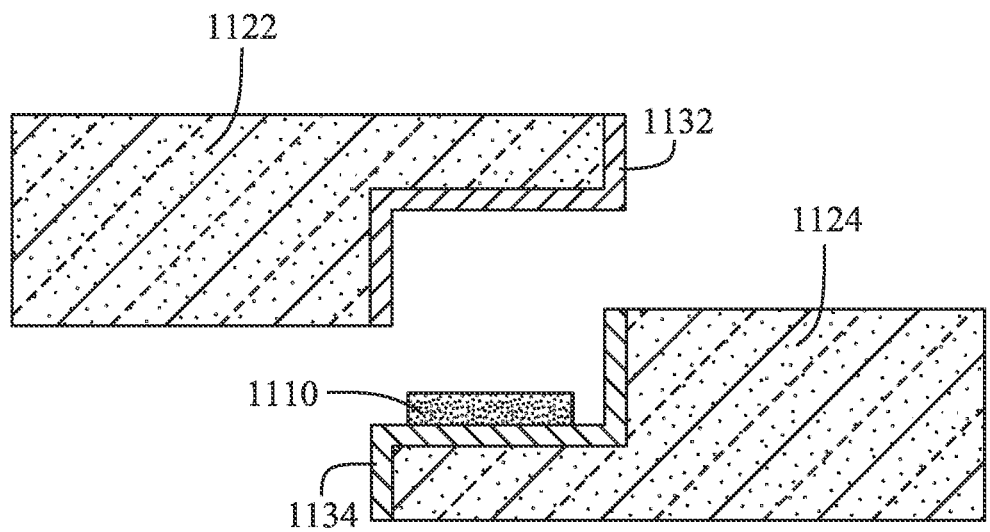
FIG. 15A shows a side cross-sectional view of two transparent portions of material that can be combined, bonded, or joined to form a unitary optical component.

FIG. 15A shows a side cross-sectional view of two transparent portions of material 1122, 1124 that can be combined, bonded, or joined to form a unitary optical component, as described herein. In some examples, the first transparent portion 1122 can have a shape corresponding to, or similar to, a first transparent portion of the final formed unitary optical component. Similarly, the second transparent portion 1124 can have a shape corresponding to, or similar to, a second transparent portion of the final formed unitary optical component. Each of the first or second transparent portions 1122, 1124 can be formed by any desired process, such as an additive or subtractive manufacturing process. In some examples, each portion 1122, 1124 can be cut or formed from a single or unitary piece of transparent material.

In some examples, one or more surfaces of the first and/or second transparent portions 1122, 1124 can be coated with an opaque material 1132, 1134. In some examples, the opaque material can include ink, metallic material, polymeric material, ceramic material, any of the opaque materials described herein, and combinations thereof. In some examples, the opaque material 1132, 1134 can be applied, deposited, or formed on the transparent portions 1122, and 1124 by spraying, printing, such as inkjet printing, stamping, vapor deposition process, such as physical or chemical vapor deposition, or any other process or combination of processes known in the art or discovered in the future. In some examples, an adhesive or other opaque material 1110 can be added to either or both of the transparent portions 1122, 1114 to bond or join the portions 1122, 1124 together. In some examples, the adhesive 1110 can be an opaque adhesive, such as an adhesive including a light-blocking or light-absorbing dye or other additive. In some examples, however, because the opaque material 1132, 1134 can serve to optically isolate the transparent portions 1122, 1124, the adhesive 1110 need to be opaque.

Figure 15B:
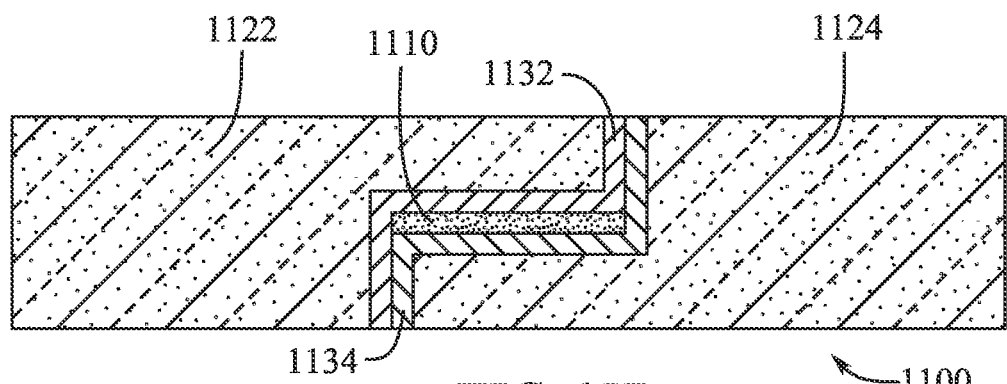
FIG. 15B shows a side cross-sectional view of the two transparent portions of material of FIG. 15A in a combined configuration.

As shown in FIG. 15B, the transparent portions 1122, 1124 can be adhered together by the adhesive 1110 in a desired configuration to form the unitary optical component 1100. In some embodiments, the unitary optical component 1100 can be similar to, or the same as, and can include some or all of the features of the unitary optical components 111, 211, 311, 400, 500, 600, 700, 811, 900, 1000 described herein.

Figure 16A:
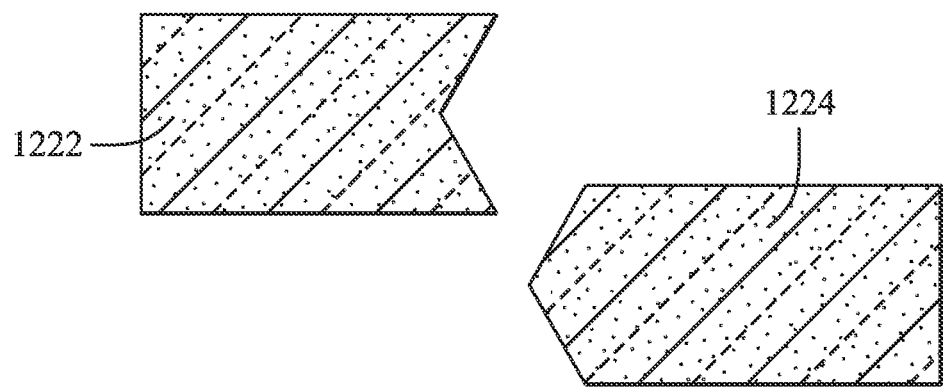
FIG. 16A shows a cross-sectional side view of a component at a stage during a formation process.
Figure 16B:
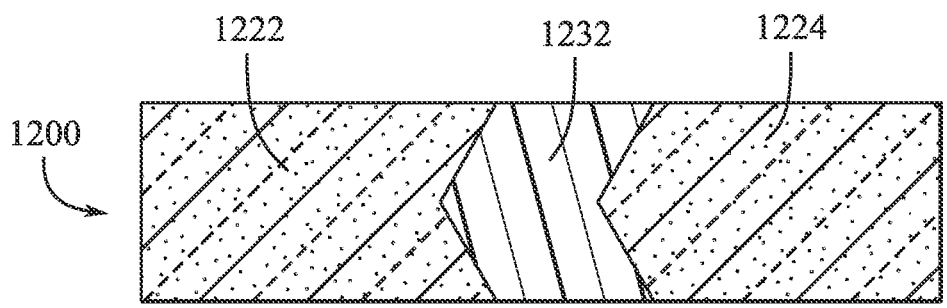
FIG. 16B shows a cross-sectional side view of a formed component.

FIG. 16A shows a cross-sectional view of transparent portions of material 1222, 1224 that can be combined, bonded, or joined to form a unitary optical component, as described herein. As with the portion 1022, 1024 described with respect to FIG. 14A, the portions of material 1222, 1224, can have shapes corresponding to, or similar to, the transparent portions of the final formed unitary optical component. Each of the first or second transparent portions 1222, 1224 can be formed by any desired process, such as an additive or subtractive manufacturing process. In some examples, each portion 1222, 1224 can be cut or formed from a single or a unitary piece of transparent material. An opaque material 1232, as shown in FIG. 16B, can be added to either or both of the transparent portions 1222, 1224 to bond, join, or fuse the transparent portions 1222, 1224 together. In some examples, the opaque material 1232 can include any of the opaque materials described herein, and can be formed into a desired shape to join the transparent portions 1222, 1224 and form the component 1200 by any desired process, such as injection molding, casting, or infilling.

FIG. 16B shows a cross-sectional view of the formed unitary optical component 1200 including the first and second transparent portion 1222, 1224 joined by the opaque portion 1232. In some embodiments, the unitary optical component 1200 can be similar to, or the same as, and can include some or all of the features of the unitary optical components 111, 211, 311, 400, 500, 600, 700, 811, 900, 1000 described herein. Further, as can be seen in FIG. 16B, the opaque portion 1232 can have one or more non-planar sidewalls. The opaque portion 1232 can include, for example, a first sidewall defining a protrusion and a second sidewall defining a recess. The opaque portion 1232 can include any desired sidewall shape or combination of sidewall shapes, for example, as can absorb or block light in a desired way or that can assist or improve the ability of the opaque portion 1232 to isolate the components below the transparent portions 1222, 1224, as described herein. In some examples, the non-planar sidewalls of the opaque portion 1232 and the transparent portions 1222, 1224 can provide a level of mechanical interlock or retention to the unitary optical component 1200. Accordingly, this mechanical interlock or interaction between the transparent portions 1222, 1224 and the opaque portion 1232 can serve to increase the strength of the unitary optical component 1200. In some examples, where the opaque portion 1232 is joined to the transparent portions 1222, 1224 with an adhesive, the combination of the adhesive and the mechanical interlock due to the non-planar sidewalls can provide a stronger bond or joint between the opaque portion 1232 and the transparent portions 1222, 1224 than a bond or joint that does not include non-planar sidewalls.

Figure 16C:
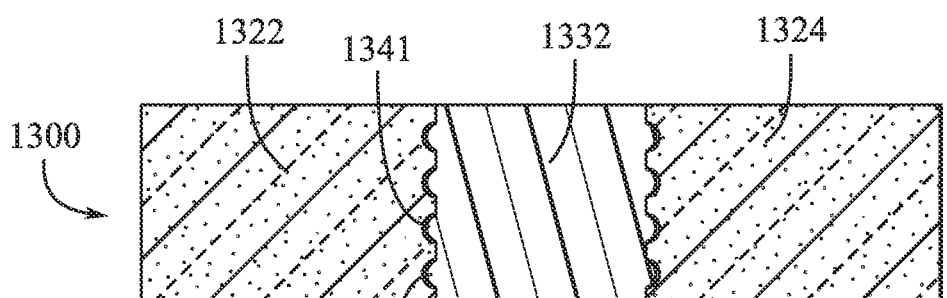
FIG. 16C shows a cross-sectional side view of a formed component.
Figure 16D:
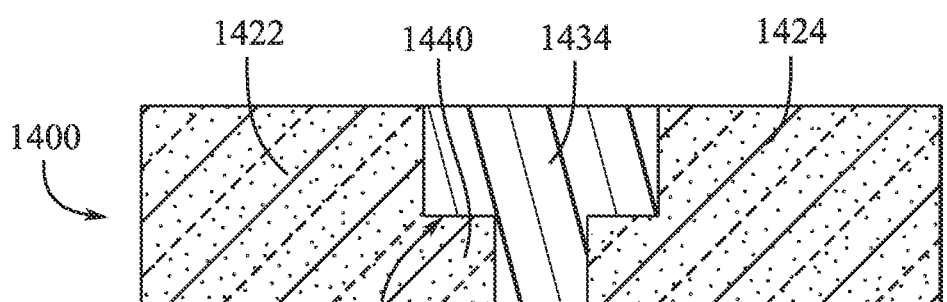
FIG. 16D shows a cross-sectional side view of a formed component.

FIGS. 16C and 16D show cross-sectional views of unitary optical components 1300, 1400 formed according to a process similar to, or the same as, a process used to form the unitary optical component 1200. In these embodiments, the opaque portions 1332, 1434 can include any desired shape or profile, for example, including non-planar sidewalls, as described herein. For example, the opaque portion 1332 can include one or more protrusions 1340, 1341 that extend therefrom. In some examples, the protrusions 1341 can be rounded or hemispherical. In some examples, these protrusions can serve to scatter incident light to further improve the optical isolation properties of the component 1300. In some examples, and as illustrated in FIG. 16D, a transparent portion 1422 can include a protrusion or a feature 1440, and the opaque portion 1434 can include a profile that corresponds to, or matches, the surface defined by the transparent portion 1422 including the protrusion 1441. In this way, the opaque portion can be bonded or fused to multiple surfaces of the transparent portions 1322, 1324, 1422, 1434. An alternative component arrangement is provided below with reference to FIGS. 17A and 17B.

Figure 17A:
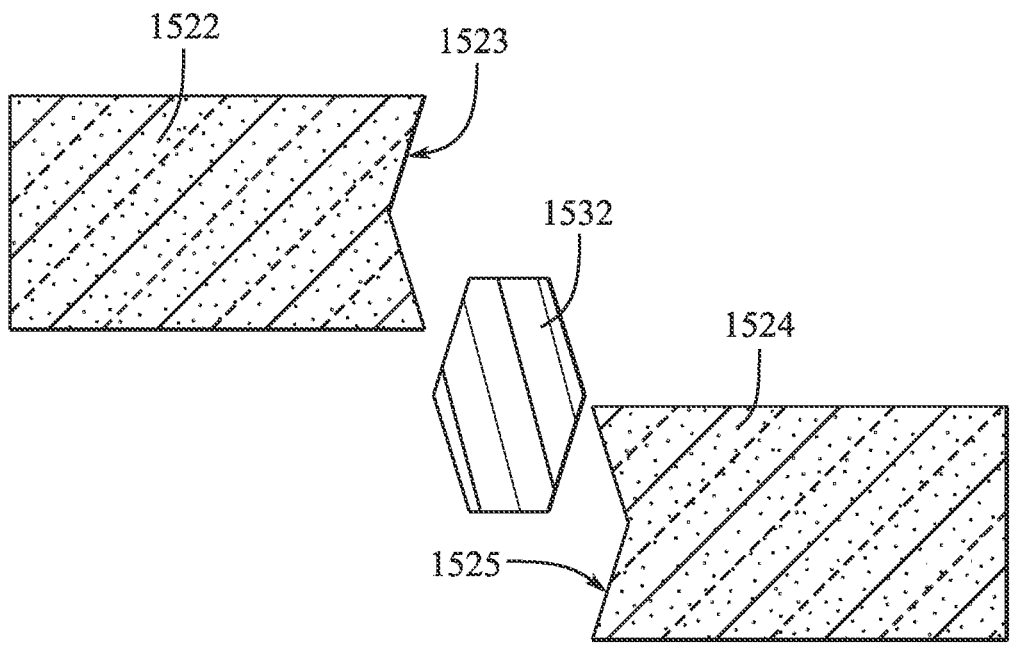
FIG. 17A shows a cross-sectional side view of a component at a stage during a formation process.

FIG. 17A shows a cross-sectional view of transparent portions of material 1522, 1524 that can be combined, bonded, or joined with an opaque portion 1532 to form a unitary optical component, as described herein. The portions of material 1522, 1524, can have shapes corresponding to, or similar to, the transparent portions of the final formed unitary optical component. Each of the first and second transparent portions 1522, 1524 can be formed by any desired process, such as an additive or subtractive manufacturing process. Further, the transparent portions 1522, 1524 can have non-planar sidewalls 1523, 1525. In this and other examples, the sidewall 1523 of the first transparent portion 1522 may not fit or align with a sidewall 1525 of the second transparent portion 1524. Accordingly, the opaque portion 1532 that can serve to join or bond the transparent portions 1522, 1524 together can have sidewalls that correspond to or have an inverse profile of the sidewalls 1523, 1525 of the first and second transparent portions 1522, 1524.

Figure 17B:
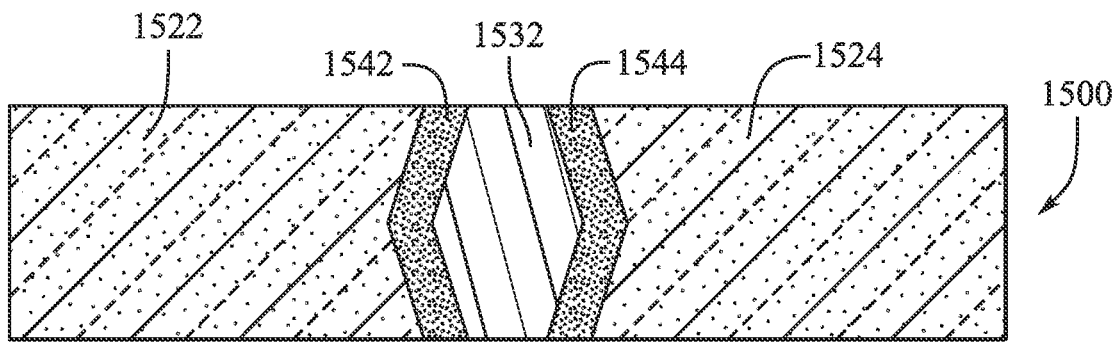
FIG. 17B shows a cross-sectional side view of a formed component.

As shown in FIG. 17B, the transparent portions 1522, 1524 can be joined together by one or more portions of adhesive 1542, 1544 in a desired configuration to form the unitary optical component 1500. In some embodiments, the unitary optical component 1500 can be similar to, or the same as, and can include some or all of the features of the unitary optical components 111, 211, 311, 400, 500, 600, 700, 811, 900, 1000, 1100, 1200, 1300 described herein. In this example, a first portion of adhesive 1542 can bond or join together the first transparent portion 1522 and the opaque portion 1532, while a second portion of adhesive 1544 can bond or join together the second transparent portion 1524 with the opaque portion 1532. In some examples, the adhesive portions 1542, 1544 can be an opaque adhesive, such as an adhesive including a light-blocking or light-absorbing dye, or other additives, as described herein. Yet another alternative component configuration is detailed below with reference to FIG. 18.

Figure 18:
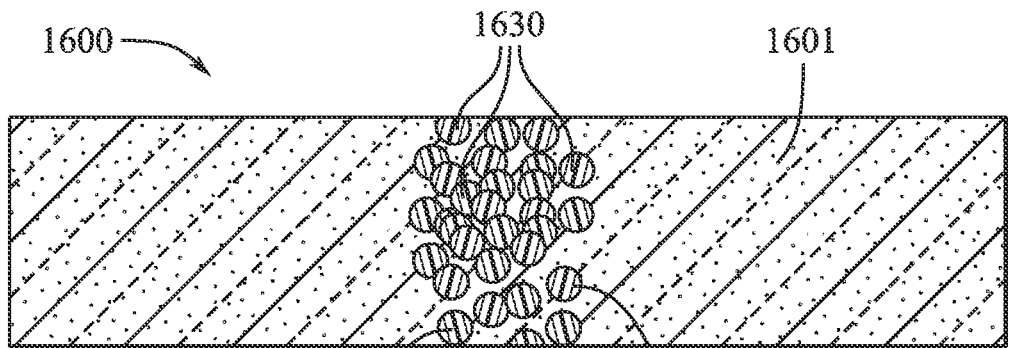
FIG. 18 shows a cross-sectional side view of a formed component.

FIG. 18 shows another example of a unitary optical component 1600 including a transparent material 1601 that can include any of the transparent materials described herein. In this example, an opaque portion can be formed in the unitary optical component 1600 by a number of opaque particles 1630 that can collectively divide the transparent material 1601 into two adjacent transparent portions, to achieve the same or similar light-blocking or optical isolation effects, as described herein with respect to other unitary optical components. The particles 1630 can include an opaque material, as described herein. While a single particle 1630 will not be able to block all total internal reflection pathways between adjacent transparent portions of the material 1601, multiple particles 1630 can together inhibit or substantially block all total internal reflection pathways between adjacent transparent portions of the material 1601. In some embodiments, the opaque particles 1630 can be rounded or spherical, although in some other embodiments, the particles 1630 can have any desired shape or size. In some examples, all of the particles 1630 can have the same shape, while in some other examples, the particles 1630 can have a variety of desired shapes.

The opaque particles 1630 can be positioned in the transparent material 1630 by any desired technique. For example, the particles 1630 can be implanted in the pre-formed transparent portion 1601 by impacting the transparent portion 1601 at high speed, by heating the transparent portion 1601 prior to impacting, by forming voids in the place of the particles 1630 and infilling the voids with opaque material, by molding the transparent material 1601 around the particles 1630, or any other manufacturing process. Additional methods for forming the desired optical component are detailed below with reference to FIGS. 19A-19C.

Figure 19A:
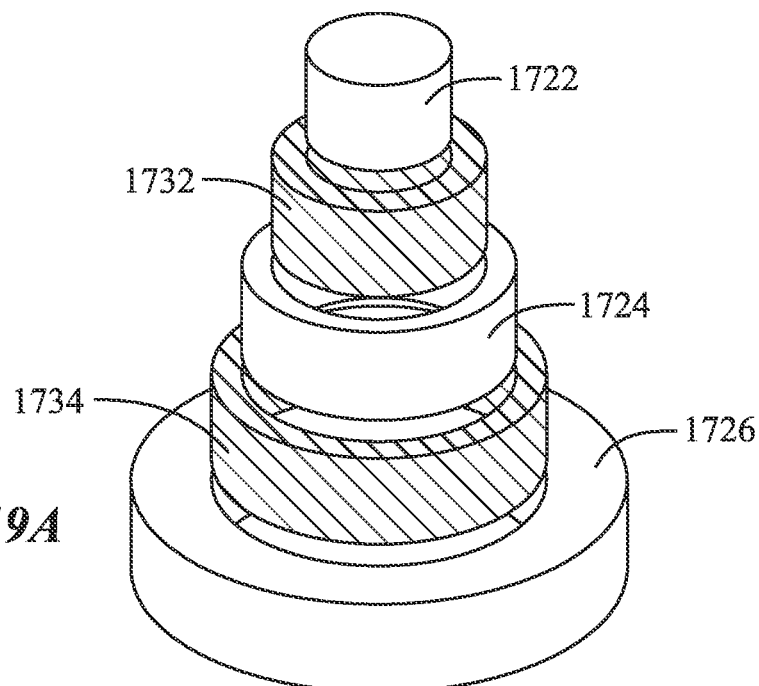
FIG. 19A shows a cutaway perspective view of a component at a stage during a formation process.
Figure 19B:
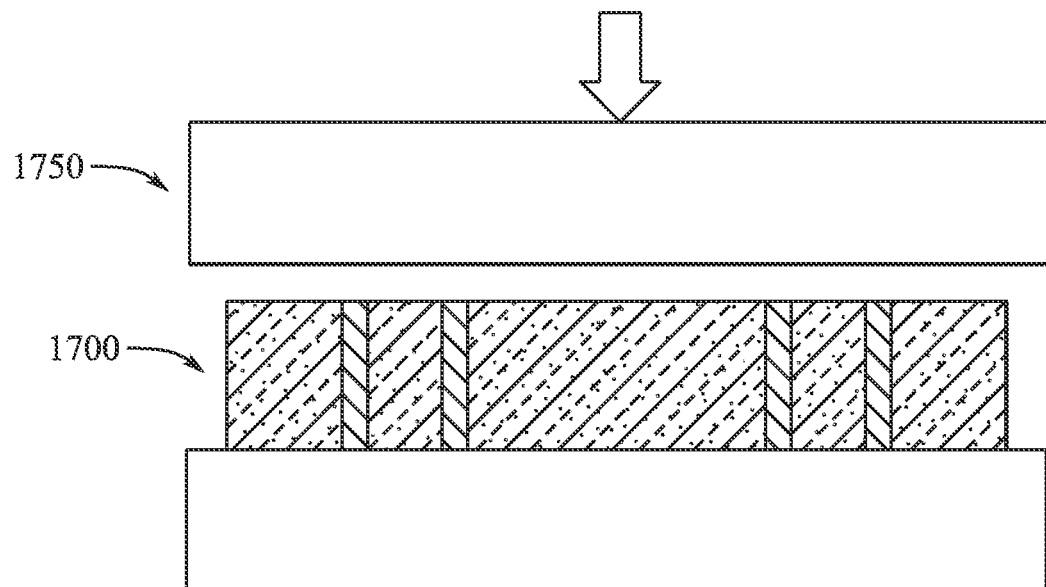
FIG. 19B shows a cross-sectional side view of a component at a stage during a formation process.
Figure 19C:
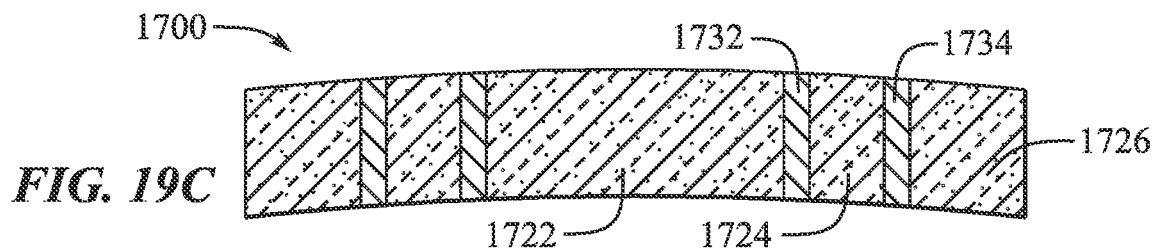
FIG. 19C shows a cross-sectional side view of a formed component.

FIGS. 19A-C shows various stages of a process for forming a unitary optical component 1700, as described herein. As shown in FIG. 19A, pre-formed transparent portions 1722, 1724, 1726 and pre-formed opaque portions 1732, 1734 can be positioned adjacent to one another in a desired configuration. In some examples, the pre-formed transparent portions 1722, 1724, 1726 and the pre-formed opaque portions 1732, 1734 can have an identical or similar shape to the transparent portions 1722, 1724, 1726 and opaque portions 1732, 1734 of the finally formed unitary optical component 1700. In some examples, the shape of any one of the pre-formed transparent portions 1722, 1724, 1726 and pre-formed opaque portions 1732, 1734 can be modified during the formation process to achieve the finally formed component 1700.

In some examples, the pre-formed transparent portions 1722, 1724, 1726 and pre-formed opaque portions 1732, 1734 are sized to be nested together and then they can be bonded or joined together by an adhesive. In some other examples, however, the pre-formed transparent portions 1722, 1724, 1726 and pre-formed opaque portions 1732, 1734 can be disposed in desired positions without yet being bonded, joined, or fused together.

The pre-formed transparent portions 1722, 1724, 1726 and pre-formed opaque portions 1732, 1734 in their desired positions can then be subjected to a desired amount of pressure by a forming tool 1750. In some examples, heat may also be applied to the component 1700 before, during, and/or after application of the pressure by the tool 1750. In some examples, the pressure can be applied from one or more desired directions, for example, a vertical direction as shown, or isostatically from all directions. In some examples, the application of pressure and/or heat by the tool 1750 can serve to bond, join, or otherwise fuse the pre-formed transparent portions 1722, 1724, 1726 and pre-formed opaque portions 1732, 1734 together. For example, the transparent and opaque portions can be joined by heating the material of each portion above a desired temperature such that adjacent portions are fused tougher, or by activating any adhesive that can be present between portions.

The formed unitary optical component 1700 is shown in FIG. 19C, including transparent portions 1722, 1724, 1726 and opaque portions 1732, 1734. As can be seen in FIG. 19C, in some examples, the tool 1750 can modify the shape of the component 1700 and one or more of the pre-formed transparent portions 1722, 1724, 1726 and pre-formed opaque portions 1732, 1734 to achieve a final shape of the unitary optical component 1700. For example, the unitary optical component 1700 can have a curved or lens shape, as described herein.

Figure 20A:
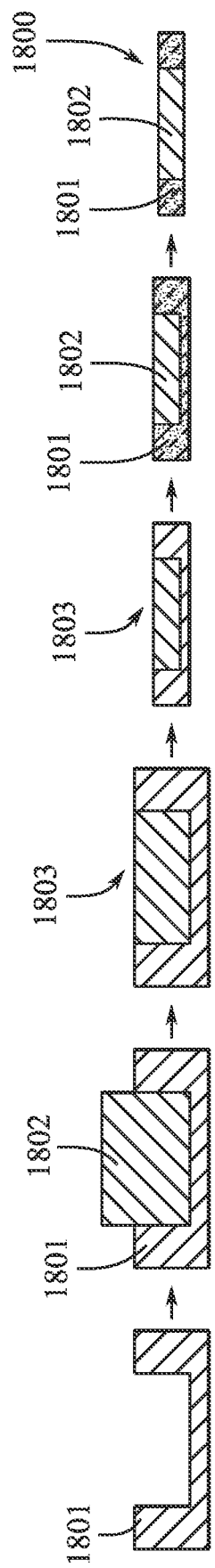
FIG. 20A shows a process flow of various stages of a process for forming a component.

FIG. 20A shows various stages of a formation process for a unitary optical component 1800, as described herein. In this example, a pre-formed portion 1801 can be provided having any desired shape. The portion 1801 can be formed by a manufacturing process, such as an additive or subtractive process, for example, injection molding. The pre-formed transparent portion 1801 can have a recess or a cavity in a desired location for an opaque portion to be formed, similar to the recesses described with respect to FIG. 13B. A portion of a second material 1802 can then be infilled into the recess formed in the transparent portion 1801 by any desired process, such as injection molding.

In some examples, where the portions 1801, 1802 can include ceramic material, each portion can be a green body formed from a molded slurry including ceramic particles. The green body 1803 including the portions 1801, 1802 can then be subjected to processing to achieve a desired shape. For example, the green body 1803 can be machined, or subjected to any desired additive or subtractive manufacturing process. In some examples, the green body 1803 can be pre-sintered prior to being formed into a desired shape. In some examples, the green body 1803 can be pressed or can be subjected to high pressure to densify or otherwise shape the material prior to a sintering or other finishing process.

Figure 20B:
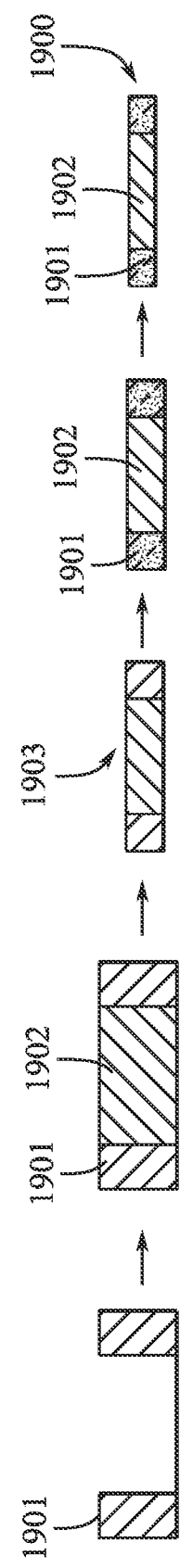
FIG. 20B shows a process flow of various stages of a process for forming a component.

In some examples, the green body 1803, can be exposed to a desired amount of heat for a desired duration, for example, as part of a sintering process. The sintering process can form the material of the green body, for example, ceramic particles, into a unitary optical component 1800, as described herein. In some examples, the initial materials of the portions 1801 and 1802 can thus be fused together as part of the sintering process, and one or more of the portions 1801, 1802 can attain their desired optical properties. For example, the portion 1801 can fail to be transparent to a desired range of wavelengths of light prior to a sintering process, but the portion 1801 can be a transparent portion 1801 as described herein, subsequent to sintering. In some examples, the unitary optical component 1801 can be subjected to further processing after sintering, for example, one or more machining, forming, or polishing processes, to achieve a final desired shape of the transparent portions or portions 1801, the opaque portion or portions 1802, and/or the unitary optical component 1800. FIG. 20B details an alternative forming process.

FIG. 20B shows various stages of a formation process for a unitary optical component 1900, as described herein. In this example, a pre-formed portion 1901 can be provided having any desired shape. The portion or portions 1901 can be formed by a manufacturing process, such as an additive or subtractive process, for example, injection molding. A portion of a second material 1902, for example, a different material or a same or similar material including one or more components selected to achieve a desired optical effect after processing, can be disposed in a desired location relative to the first portion 1901. In some examples, where the portions 1901, 1902 can include ceramic material, the portions can combine to be a green body 1903 formed from a molded slurry including ceramic particles.

In some examples, the green body 1903, can be exposed to a desired amount of heat for a desired duration, for example, as part of a sintering process. The sintering process can form the material of the green body, for example, ceramic particles, into a unitary optical component 1900, as described herein. In some examples, the initial materials of the portions 1901 and 1902 can be fused together as part of the sintering process. Subsequent or concurrent with a sintering process, the green body 1903 can be subjected a desired level of pressure and/or heat, for example, during a hot isostatic pressing process. In some examples, the hot isostatic pressing process can further densify the material of the portions 1901, 1902. In some examples, the hot isostatic pressing process can result in one or more of the portions 1901, 1902 attaining their desired optical properties. For example, the hot isostatic pressing process can result in the material of the portion 1901 being transparent to a desired range of wavelengths of light and/or the portion 1902 being opaque to a desired range of wavelengths of light. The formed component can then be subjected to any number of finishing processes, such as a polishing process or a double-sided polishing process, to form the final unitary optical component 1900 as described herein. Additional methods for manufacturing the unitary optical components are detailed below with reference to FIGS. 21A and 21B.

Figure 21A:
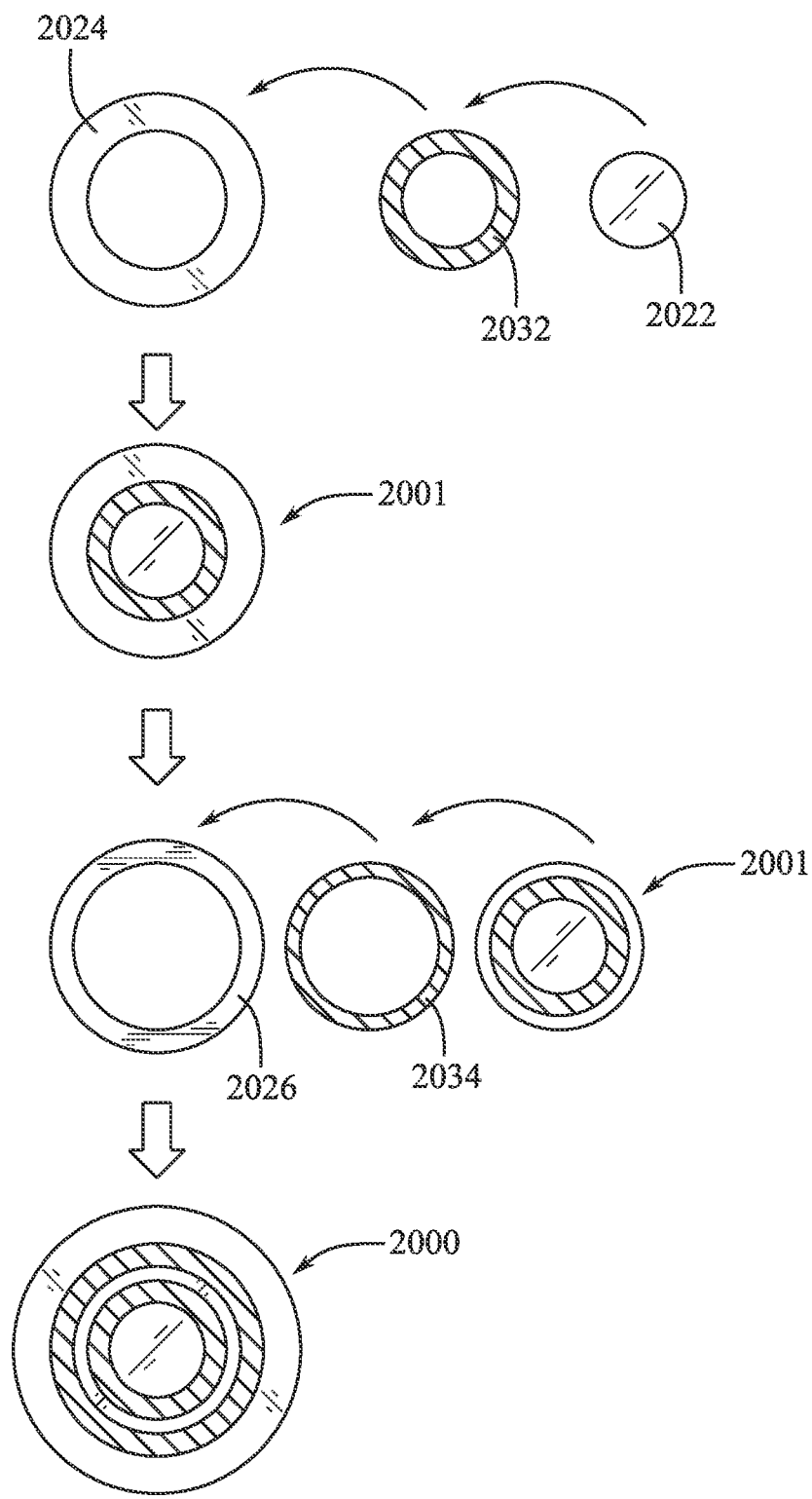
FIG. 21A shows a process flow of various stages of a process for forming a component.

FIG. 21A shows various stages of a formation process for one or more unitary optical components 2000, as described herein. The formation process illustrated in FIG. 21A can be considered a redrawing process, and in some cases, the materials of the transparent portions 2022, 2024, 2026 and the opaque portions 2032, 2034 can be a ceramic material, for example, glasses having the desired optical properties of the transparent and opaque portions described herein. In some examples, the transparent portions 2022, 2024, 2026 and the opaque portions 2032, 2034 can be glass rods that can include an aperture or a through-hole.

In some examples, the first transparent portion 2022 can be disposed within the first opaque portion 2032, and the first transparent portion 2022 and first opaque portion 2032 can be disposed in the second transparent portion 2024 to form an optical part 2001. The optical part 2001 can be subjected to a re-drawing process, for example, including heating the optical part 2001 to an elevated temperature, and forcing the part 2001 through a die to bond the first and second transparent portions 2024 and the opaque portion 2032 together. After being subjected to the re-drawing process, the optical part 2001 can be subjected to further processing, such as a surface polish, to achieve desired optical properties.

After any optional processing, the second opaque portion 2034 can be disposed around the re-drawn optical part 2001, and the third transparent portion 20026 can be disposed around the second opaque portion 2034 and the re-drawn optical part 2001. These components can then be subjected to an additional re-drawing process, for example, including elevated temperatures and forcing the components through a die to bond them together. After this second re-drawing process, the components can be fused together into the final unitary optical component 2000 including transparent portions 2022, 2024, 2026 and the opaque portions 2032, 2034. In some examples, the re-drawn unitary component 2000 can be subjected to any desired further processing, such as polishing, cutting, slicing, or other processes.

Figure 21B:
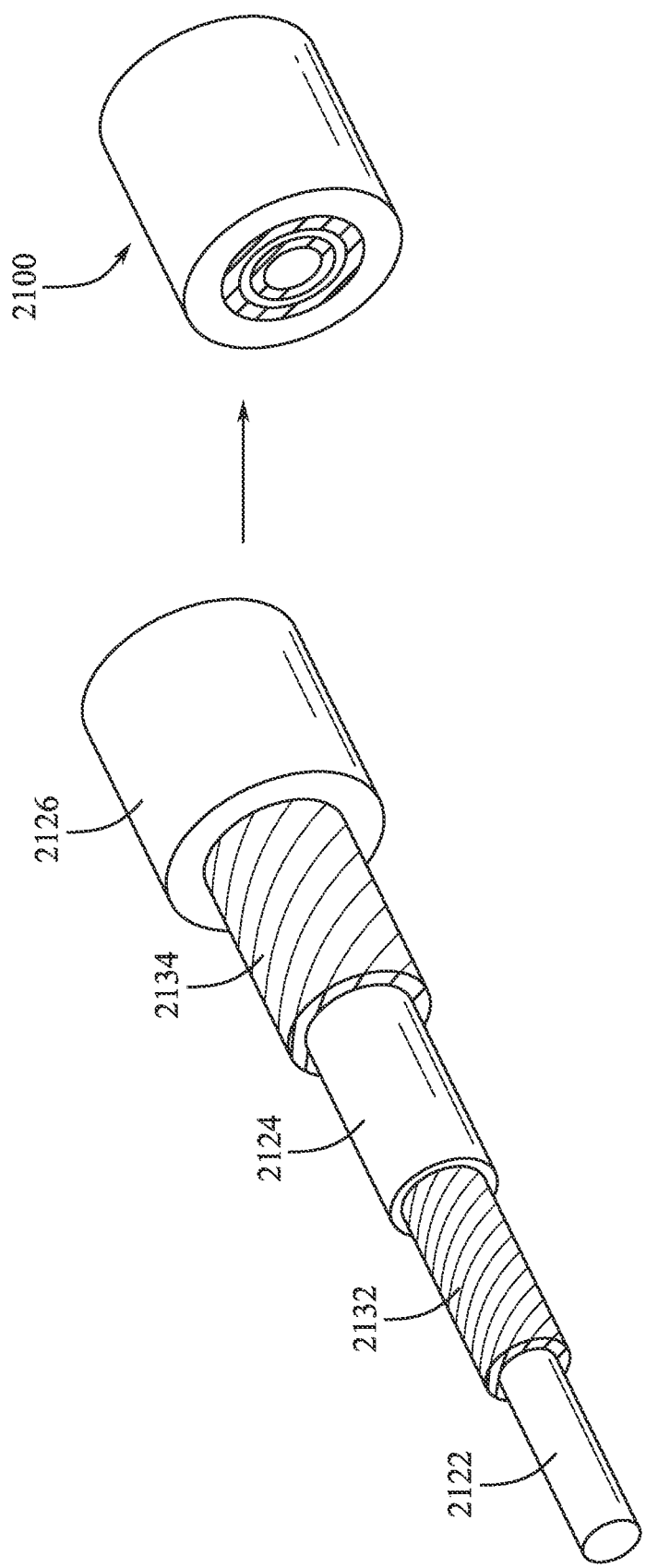
FIG. 21B shows a process flow of various stages of a process for forming a component.

FIG. 21B shows a perspective view of individual transparent portions 2122, 2124, 2126 and the opaque portions 2132, 2134 prior to being subjected to a double re-drawing process, such as the process described with respect to FIG. 21A, as well as the formed unitary optical component 2100 after the double re-drawing process. As can be seen, where the individual transparent portions 2122, 2124, 2126 and the opaque portions 2132, 2134 include rods including through-holes or apertures, the unitary optical component 2100 formed by a double re-drawing process can have a height or thickness corresponding to, or greater than, the height or thickness of the rods comprising the individual transparent portions 2122, 2124, 2126 and the opaque portions 2132, 2134. Accordingly, in some examples, the unitary optical component 2100 can be cut or sliced into any number of desired unitary optical components having a desired height or thickness.

Any of the features or aspects of the components discussed herein can be combined or included in any varied combination. For example, the design and shape of the unitary optical component is not limited in any way and can be formed by any number of processes, including those discussed herein. A component including one or more transparent portions and one or more opaque portions, as discussed herein, can be or can form all or a portion of a component, such as a housing or enclosure, for an electronic device. The component can also be or form any number of additional components of an electronic device, including internal components, external components, cases, surfaces, or partial surfaces.

To the extent applicable to the present technology, gathering and use of data available from various sources can be used to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, TWITTER® ID's, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to calculated control of the delivered content. Further, other uses for personal information data that benefit the user are also contemplated by the present disclosure. For instance, health and fitness data may be used to provide insights into a user's general wellness or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services or anytime thereafter. In another example, users can select not to provide mood-associated data for targeted content delivery services. In yet another example, users can select to limit the length of time mood-associated data is maintained or entirely prohibit the development of a baseline mood profile. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publicly available information.

As used herein, the terms exterior, outer, interior, inner, top, and bottom are used for reference purposes only. An exterior or outer portion of a component can form a portion of an exterior surface of the component but may not necessarily form the entire exterior of outer surface thereof. Similarly, the interior or inner portion of a component can form or define an interior or inner portion of the component but can also form or define a portion of an exterior or outer surface of the component. A top portion of a component can be located above a bottom portion in some orientations of the component, but can also be located in line with, below, or in other spatial relationships with the bottom portion depending on the orientation of the component.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. An electronic device, comprising:
   a housing defining an aperture and at least partially defining an internal volume of the electronic device;
   a first electromagnetic radiation emitter disposed in the internal volume;
   a second electromagnetic radiation emitter disposed in the internal volume;
   an electromagnetic radiation detector disposed in the internal volume;
   an optical component disposed in the aperture, the optical component comprising:
   a first transparent portion disposed above the first electromagnetic radiation emitter;
   a second transparent portion disposed above the second electromagnetic radiation emitter;
   a third transparent portion disposed above the electromagnetic radiation detector; and
   a first opaque portion surrounding the first transparent portion, a second opaque portion surrounding the second transparent portion, the first and second opaque portions comprising sidewalls, the first transparent portion, the second transparent portion, the third transparent portion, and the first and second opaque portions defining a flush exterior surface of the electronic device and an interior surface of the optical component, the first and second opaque portions extending from the exterior surface to the interior surface;
   a first isolation protrusion disposed in the internal volume between a first chamber and a second chamber, the first isolation protrusion abutting the optical component and at least partially defining the first chamber and the second chamber; and
   a second isolation protrusion disposed in the internal volume between the first chamber and a third chamber, the second isolation protrusion abutting the optical component and at least partially defining the first chamber and the third chamber;

wherein:
the first electromagnetic radiation emitter is disposed in the first chamber, the second electromagnetic radiation emitter is disposed in the second chamber, and the electromagnetic radiation detector is disposed in the third chamber;
the first isolation protrusion and the second isolation protrusion prevent electromagnetic radiation from passing between the first chamber, the second chamber, and the third chamber within the internal volume; and
the first isolation protrusion comprises sidewalls aligned with the sidewalls of the first and second opaque portions and the second isolation protrusion comprises sidewalls aligned with the sidewalls of the first and third opaque portions.

2. The electronic device of claim 1, wherein the first electromagnetic radiation emitter comprises a light emitting diode.

3. The electronic device of claim 1, wherein the electromagnetic radiation detector comprises at least one of a visible light detector or an infrared light detector.

4. The electronic device of claim 1, wherein the electromagnetic radiation detector and the first electromagnetic radiation emitter are separate from the optical component.

5. The electronic device of claim 1, wherein the second electromagnetic radiation emitter is disposed under the second transparent portion.

6. The electronic device of claim 1, further comprising an isolation component disposed in the internal volume, the isolation component abutting the optical component and at least partially defining the first chamber and the second chamber;
wherein:
the electromagnetic radiation detector is disposed in the first chamber and the first electromagnetic radiation emitter is disposed in the second chamber; and
the isolation component prevents electromagnetic radiation from passing between the second chamber and the first chamber within the internal volume.

7. The electronic device of claim 6, wherein the isolation component abuts the optical component at the first opaque portion.

8. A housing for an electronic device, comprising:
a body defining an aperture and at least partially defining an exterior surface of the electronic device;
an optical component disposed in the aperture, the optical component comprising:
a first transparent portion and a second transparent portion, the second transparent portion isolated from the first transparent portion by a first opaque portion surrounding the first transparent portion and a second opaque portion surrounding the second transparent portion;
a third transparent portion, the first opaque portion and the second opaque portion disposed between the first transparent portion, the second transparent portion, and the third transparent portion;
the first transparent portion, the second transparent portion, the third transparent portion, the first opaque portion, and the second opaque portion further defining the exterior surface of the electronic device and defining an interior surface of the optical component; and
an isolation component comprising a first protrusion centrally aligned with the first opaque portion and a second protrusion centrally aligned with the second opaque portion;

wherein:
the first transparent portion, the second transparent portion, and the third transparent portion define a larger surface area of the exterior surface than the first opaque portion and the second opaque portion; and
the first opaque portion and the second opaque portion extend from the exterior surface to the interior surface.

9. The housing of claim 8, wherein the first transparent portion is disposed over a first electromagnetic radiation emitter.

10. The housing of claim 8, wherein the second transparent portion is disposed over a second electromagnetic radiation emitter.

11. The housing of claim 8, wherein the third transparent portion is disposed over an electromagnetic radiation detector.

12. The housing of claim 8, wherein the first transparent portion, the second transparent portion, the third transparent portion, the first opaque portion, and the second opaque portion comprise ceramic material.

13. The housing of claim 8, wherein at least one of the first opaque portion or the second opaque portion comprises a coating deposited onto a surface of an adjacent transparent portion.

14. The housing of claim 8, wherein at least one of the first transparent portion, the second transparent portion, or the third transparent portion is joined to at least one of the first opaque portion or the second opaque portion by an adhesive.

15. The housing of claim 8, wherein at least one of the first transparent portion, the second transparent portion, or the third transparent portion is directly fused to at least one of the first opaque portion or the second opaque portion.

16. The housing of claim 8, wherein at least one of the first opaque portion or the second opaque portion comprises a non-planar sidewall.

17. The housing of claim 8, wherein at least one of the first opaque portion or the second opaque portion comprises a first section defining the exterior surface and a second section defining the interior surface, the first section being laterally offset from the second section.

18. An electronic device, comprising:
a housing defining an aperture and at least partially defining an internal volume of the electronic device;
an electromagnetic radiation emitter disposed in the internal volume;
an electromagnetic radiation detector disposed in the internal volume;
an optical component disposed in the aperture, the optical component comprising:
a first transparent portion disposed above the electromagnetic radiation emitter;
a second transparent portion disposed above another electromagnetic radiation emitter;
a first opaque portion surrounding the first transparent portion and a second opaque portion surrounding the second transparent portion;
a third transparent portion disposed above the electromagnetic radiation detector;
the third transparent portion isolated from the first transparent portion by the first opaque portion and isolated from the second transparent portion by the second opaque portion;
the first transparent portion, the second transparent portion, the third transparent portion, the first opaque portion, and the second opaque portion at least partially defining an exterior surface of the electronic device and an interior surface of the optical component; and an isolation component disposed in the internal volume;

wherein:

the first transparent portion, the second transparent portion, and the third transparent portion define a larger surface area of the exterior surface than the first opaque portion and the second opaque portion;

the first opaque portion and the second opaque portion extend from the exterior surface to the interior surface;

the isolation component comprises a first protrusion adjacent the first opaque portion and a second protrusion adjacent the second opaque portion; and a shape of a distal portion of the first protrusion corresponds to a shape of the first opaque portion and a shape of a distal portion of the second protrusion corresponds to a shape of the second opaque portion.

19. The electronic device, of claim 18, wherein the first opaque portion and the second opaque portion comprise a conductive material.

20. The electronic device of claim 18, wherein the optical component is formed by a double redrawing process.

* * * * *